(12) United States Patent
Barbour et al.

(10) Patent No.: US 11,482,305 B2
(45) Date of Patent: Oct. 25, 2022

(54) ARTIFICIAL INTELLIGENCE ANALYSIS OF RNA TRANSCRIPTOME FOR DRUG DISCOVERY

(71) Applicant: SF17 THERAPEUTICS, INC., Oakland, CA (US)

(72) Inventors: Jason Barbour, Oakland, CA (US); David Ott, San Francisco, CA (US)

(73) Assignee: Synkrino Biotherapeutics, Inc., Oakland, CA (US)

( * ) Notice: Subject to any disclaimer, the term of this patent is extended or adjusted under 35 U.S.C. 154(b) by 0 days.

(21) Appl. No.: 16/643,511

(22) PCT Filed: Aug. 19, 2019

(86) PCT No.: PCT/US2019/047078
§ 371 (c)(1),
(2) Date: Feb. 28, 2020

(87) PCT Pub. No.: WO2020/041204
PCT Pub. Date: Feb. 27, 2020

(65) Prior Publication Data
US 2021/0183472 A1   Jun. 17, 2021

Related U.S. Application Data

(60) Provisional application No. 62/719,614, filed on Aug. 18, 2018.

(51) Int. Cl.
*G16B 40/20* (2019.01)
*G16B 50/50* (2019.01)
*G16B 20/00* (2019.01)
*G16B 30/20* (2019.01)

(52) U.S. Cl.
CPC ............. *G16B 40/20* (2019.02); *G16B 20/00* (2019.02); *G16B 30/20* (2019.02); *G16B 50/50* (2019.02)

(58) Field of Classification Search
CPC ......... G16B 40/20; G16B 20/00; G16B 30/20
See application file for complete search history.

(56) References Cited

U.S. PATENT DOCUMENTS

| | | |
|---|---|---|
| 8,775,092 B2 | 7/2014 | Colwell et al. |
| 10,185,803 B2 | 1/2019 | Frey et al. |
| 10,262,107 B1 | 4/2019 | Tran et al. |
| 2006/0259246 A1 | 11/2006 | Huyn |
| 2007/0072232 A1 | 3/2007 | Stanton |
| 2015/0066378 A1 | 3/2015 | Robison et al. |
| 2016/0068915 A1 | 3/2016 | Kennedy et al. |
| 2018/0163261 A1 | 6/2018 | Zeigler et al. |
| 2018/0165412 A1 | 6/2018 | Frey et al. |
| 2019/0019581 A1 | 1/2019 | Vaughan et al. |
| 2019/0114391 A1 | 4/2019 | Jaganathan et al. |
| 2019/0164632 A1 | 5/2019 | Jung et al. |
| 2019/0172588 A1 | 6/2019 | Tran et al. |
| 2019/0252041 A1 | 8/2019 | Frey et al. |

FOREIGN PATENT DOCUMENTS

| | | |
|---|---|---|
| CA | 2894317 A1 | 12/2016 |
| CN | 109273098 A | 1/2019 |
| WO | 2019/000329 A1 | 1/2019 |
| WO | 2019/084559 A1 | 5/2019 |
| WO | 2019/148141 A1 | 8/2019 |

OTHER PUBLICATIONS

Lopes-Ramos et al., Comprehensive evaluation of the effectiveness of gene expression signatures to predict complete response to neoadjuvant chemoradiotherapy and guide surgical intervention in rectal cancer, 2015, 208, p. 319-326 (Year: 2015).*
Abbas et al., A Review of Computational Methods for Finding Non-Coding RNA Genes, 2016, Genes, 7:113, p. 1-14 (Year: 2016).*
International Search Report in PCT Application No. PCT/US19/47078, dated Dec. 3, 2019.

* cited by examiner

*Primary Examiner* — Olivia M. Wise
*Assistant Examiner* — Kaitlyn L Minchella
(74) *Attorney, Agent, or Firm* — Cognition IP, P.C.; Edward Steakley

(57) ABSTRACT

A system and method may be provided to receive sample RNA reads from patients and generate lists of genes and their associated RNA expression levels in each patient. Some of the RNA reads may be matched to an RNA transcript or gene or gene family in terms of their match likelihood and other RNA reads may be matched to an RNA transcript or gene or gene family through the use of one or more machine learning classifiers. A machine learning classifier may be trained based on the plurality of the lists and a plurality of corresponding patients' clinical status data to identify gene patterns that recur with a high degree of frequency in the plurality of the lists. Those gene patterns can be capable of modifying a disease or treatment response and can be targeted for drug/treatment development.

24 Claims, 24 Drawing Sheets
Specification includes a Sequence Listing.

FIG. 5

ARTIFICIAL INTELLIGENCE ANALYSIS OF RNA TRANSCRIPTOME FOR DRUG DISCOVERY

CROSS-REFERENCE TO RELATED APPLICATIONS

This application claims the benefit of U.S. Provisional Patent Application No. 62/719,614, filed Aug. 18, 2018, which is hereby incorporated by reference in its entirety.

Incorporation-by-Reference of Sequence Listing or Table

The material in the accompanying sequence listing is hereby incorporated by reference in its entirety into this application, and forms part of the disclosure. The accompanying file, named SequenceListing.txt was created on Jun. 9, 2022 and is 15 KB. The file can be accessed using Microsoft Word on a computer that uses Windows OS.

FIELD OF INVENTION

The present disclosure relates generally to identifying and quantifying RNA transcripts from a set of RNA fragments and using the identity and quantity of RNA transcripts along with disease or treatment response data to identify gene patterns capable of modifying the disease and/or the treatment response.

BACKGROUND

RNA sequencing may be performed on a biological sample of a patient to identify RNA present in the sample. RNA sequencing may be performed using high-throughput sequencing, which may also be referred to as next-generation sequencing, which may sequence RNA transcripts more quickly and accurately than prior methods. In some instances of high-throughput sequencing, such as Illumina sequencing, RNA transcripts are cut into shorter fragments that allow the shorter fragments to be sequenced more quickly. However, generally, as the fragments often lack any annotation or other label or identifying information, it is not clear how to re-assemble the shorter fragments, called RNA reads, back into the original RNA transcripts that they came from.

The set of RNA transcripts that are present in a patient sample at a given time, sometimes referred to as the RNA transcriptome, provides a dynamic window into cell activity at the time the sample was taken. The RNA transcriptome may comprise total RNA or specific subpopulations of RNA such as mRNA, miRNA, tRNA, ribosomal RNA, and others. Unlike DNA, which is static, the presence of RNA can provide insights into the actions and choices, so to speak, that a cell was making just before it was removed from the body.

SUMMARY

Some embodiments disclosed herein relate to reconstructing an RNA transcriptome from a set of RNA reads, where the RNA reads may be the output of high-throughput sequencing. Moreover, some embodiments relate to a method of identifying a gene of interest in a disease or treatment response by training a machine learning classifier on a training set of RNA transcriptome data and indications of whether the corresponding patients have a disease or treatment response of interest. In some embodiments, a treatment response of interest is a failure to respond to conventional or standard therapies. In some embodiments, the gene of interest may be a gene pattern recurring with high degree of frequency in a patient population, and wherein the gene pattern is capable of modifying the course of the disease or patient treatment response.

In an embodiment, a list of sequenced RNA reads from a sample of a patient is provided and a dictionary of RNA transcripts is provided. The RNA reads may be matched to RNA transcripts in the dictionary. A first plurality of RNA reads may be matched to a corresponding RNA transcript by this mechanism. For a second plurality of RNA reads no matching corresponding RNA transcript is found. Each of the second plurality of RNA reads may be input into one or more machine learning classifiers, which categorize each of the second plurality of RNA reads to a gene or gene family. RNA transcripts may be identified from the first plurality of RNA reads by methods of indexing such as use of hashing, De Bruijn graphs, and/or matching RNA reads to RNA scaffolds. RNA transcripts may be assembled from the second plurality of RNA reads by stitching together RNA reads that match the same RNA transcript or gene or gene family and have a matching RNA sequence, such as at an end of the read. A training set may be created including these RNA transcripts, comprising an RNA transcriptome, and the RNA transcriptomes of other patients, along with an indication of whether each patient has or does not have a disease or treatment response of interest. A disease/response machine learning classifier is trained using this training set to identify gene patterns capable of modifying the disease or treatment response, based on an input set of RNA transcripts. In an embodiment, the classifier is a random forest classifier. The parameters of the disease/response prediction machine learning classifier, and a parameter of the disease/response prediction machine learning classifier may be used to identify an RNA transcript or gene or gene family of interest in the disease or treatment response, where the interest comprises capability of the gene to modify the disease and/or the treatment response.

In an embodiment, the disease/response prediction machine learning classifier, or a portion thereof, may be used to diagnose new patients. An RNA transcriptome of a new patient may be generated as described above and input into the disease/response prediction machine learning classifier, or portion thereof, to output a prediction of whether the patient has the disease or treatment response of interest.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein:

FIG. 5 illustrates an exemplary list of RNA reads output by the high-throughput sequencing process.

DETAILED DESCRIPTION

Figure 1A:
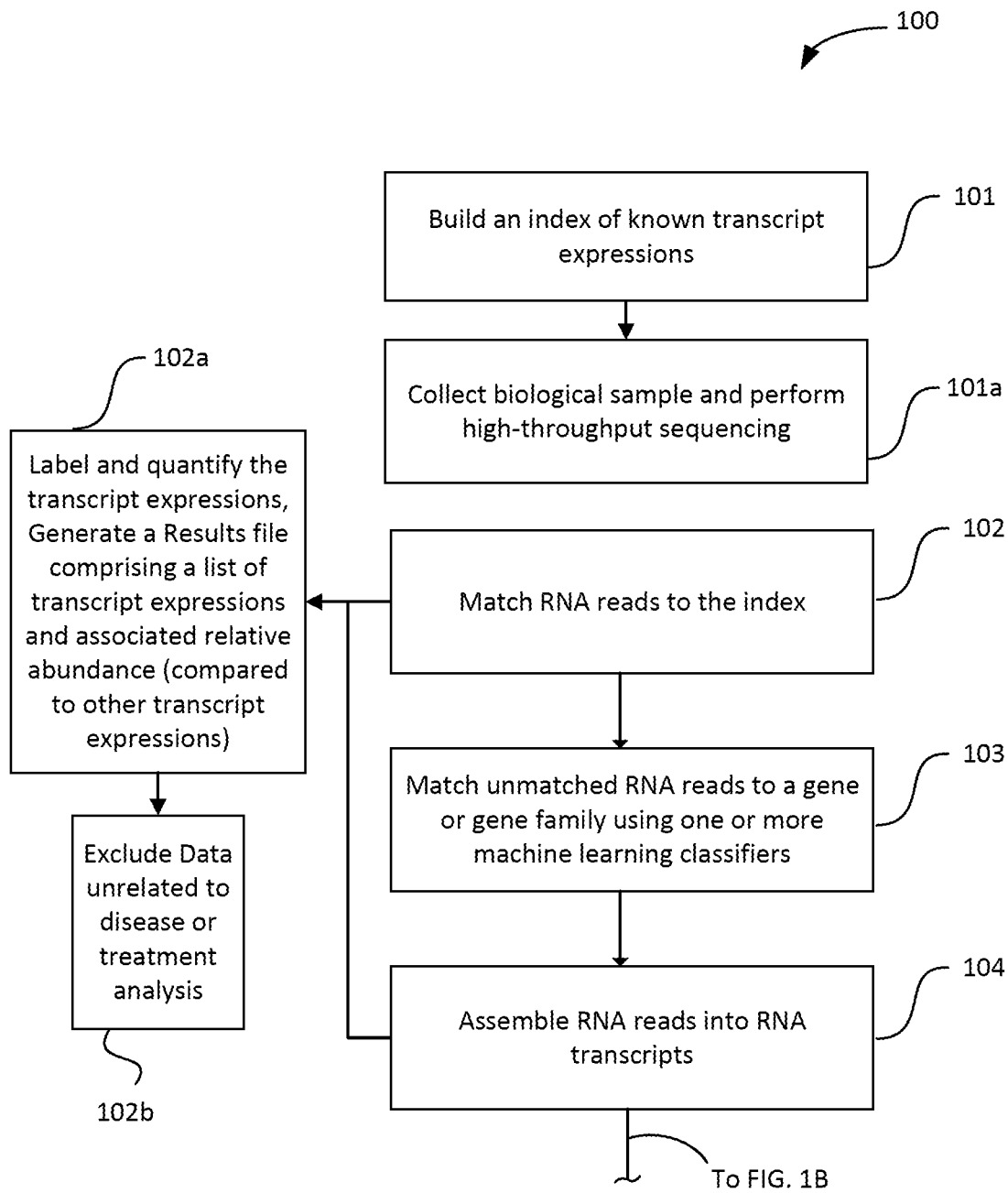
FIG. 1A illustrates an exemplary method for analysis of the RNA transcriptomes of a plurality of patients, which may be used in one embodiment.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

FIG. 1A illustrates an exemplary computer-implemented method 100 for analysis of the RNA transcriptomes of a plurality of patients and the patients' associated disease data and/or clinical status to determine one or more recurring patterns of interest in the patients. The patterns of interest can indicate a correspondence between a gene pattern and failure to respond to a treatment. In one embodiment, the gene patterns corresponding to failure to respond to a treatment can be used for further study and analysis in laboratory and/or clinical settings for developing drugs that target that gene pattern.

The presence and quantity of RNA transcripts is related to the genes of the patient. Certain RNA transcripts, such as messenger RNA (mRNA), are associated with and correspond to a gene, such as the gene from which the RNA transcript is transcribed from DNA in the chromosome of a cell, for example, an immune system cell. In some cases, knowing the gene involved allows determining a corresponding RNA transcript or transcripts to the gene. Vice versa, knowing the sequence of an RNA transcript may allow identification of the corresponding gene. The relationships between genes and RNA transcripts may be stored in RNA transcript dictionaries, which are also sometimes referred to as RNA transcript libraries. Moreover, genes may be related to each other in hierarchical gene families, with one gene family encompassing multiple variations of a gene. Isoforms are examples of related forms of the same gene.

Additionally, studying drug target gene patterns or human diseases can be made more effective by analyzing the RNA transcripts of a gene. One gene can be expressed in a multitude of ways, by a process referred to as reshuffling, where RNA transcripts can skip, rearrange or repeat, DNA exons, to generate different expressions. Those expressions can generate different proteins. As a result, to effectively study diseases and responses to treatment, RNA transcripts can provide a better and more comprehensive approach.

In step 101, an index of known transcript expressions can be built to help identify RNA reads. The index is a reference list of RNA transcripts and/or transcript expressions that have been identified in a human cellular transcriptomics. In one embodiment, the index can be generated from a list provided by the National Center for Biotechnology Information (NCBI).

In step 101a, a biological sample is collected from a patient and high-throughput RNA sequencing is performed on the sample to sequence the RNA transcripts present in the cells of the sample. One method of high-throughput sequencing that may be used is Illumina sequencing. In some embodiments of the high-throughput sequencing process, the RNA transcripts are cut into shorter fragments called reads, and the nucleotides of each of the fragments is sequenced and recorded in a text file. The RNA reads thus form smaller portions of the original RNA transcripts in the sample. The text file may be compressed into a binary format for storage, and uncompressed when needed for analysis.

In step 102, methods of analyzing the RNA reads may be performed in order to identify the underlying RNA transcripts that were present in the sample and their absolute or relative quantity. In an embodiment, at least some of the RNA reads are matched to the RNA transcripts from which they were created by using methods of indexing. Various approaches may be used. For example, the RNA transcripts in the index can be transformed into one or more De Bruijn graphs. RNA reads may be used to find a match in the index by walking the De Bruijn graph until a confident match with a known transcript expression in the De Bruijn graph is identified. The details of finding a match with the index file will further be described in relation to the embodiment of FIG. 12.

Other methods of matching RNA reads to an index, reference or dictionary can also be effectively used. The matched RNA reads can be used to generate a Results file, which may be any kind of data structure. The Results file can include a list of transcript expressions and their associated relative or absolute abundances in the sample compared to other transcript expressions. In other words, the Results file is a list of identified, annotated and quantified transcript expressions for a patient. In one embodiment, a maximum likelihood estimation method alone or in combination with walking the De Bruijn graph can be used to generate relative or absolute abundances of identified transcript expressions (the Results file). In another embodiment, Bayesian methods alone or in combination with walking the De Bruijn graph can be used to generate the Results file. In other words, statistical methods (including maximum likelihood estimation and Bayesian methods) may be used for RNA reads that may mapped to more than RNA transcript, in order to estimate RNA transcript expression levels more precisely.

In an embodiment, RNA reads are matched to known RNA transcripts by hashing the RNA reads to a dictionary of RNA transcripts. A hash function is computed on the entire RNA read, or a portion of the RNA read, to match it to a location of in a hash table. The hash table contains the known RNA transcripts that contain the subsequence matching the RNA read. In some cases, a single RNA transcript matches the RNA read, if the RNA read is chosen to be sufficiently long. As a result, the RNA read is matched to a known RNA transcript.

In an embodiment, the RNA reads are compared to the RNA transcripts by edit distance. Edit distance is a measure of the number of edits that must be made to one sequence to make it identical to the other match, where edits may include, for example, deletions, insertions, or modifications. This allows for small changes to have occurred in the RNA read such as by mutation of sequencing error. The RNA transcript that has the closest edit distance to the RNA read is selected as the match. In an embodiment, an RNA transcript with an edit distance below a threshold to the RNA read is selected as the match.

In an embodiment, the RNA reads may be scanned left to right and portions selected at intervals. All or fewer than all portions of the RNA read may be used. The portions selected from a single RNA read may be looked up in a dictionary that matches RNA portions to RNA transcripts containing those portions. Upon performing the look up process for a plurality of RNA portions, a candidate set of RNA transcripts may be determined. Based on the intersection of the candidate RNA transcripts, where the intersection identifies RNA transcripts that appear for all or most of the RNA portions, a corresponding RNA transcript is determined for the RNA read.

At step 102b, some RNA reads and their associated RNA transcripts can be excluded from further consideration and processing. For example, some known patterns of RNA transcript can correspond to patterns, which do not contribute information for disease prediction or treatment planning. For example, many RNA transcripts may correspond to hemoglobin cells, where a particular drug discovery effort may not be targeting. Other example data marked for exclusion can include RNA transcripts from viruses, bacteria or non-human RNA source. Additionally, RNA reads and associated transcripts can be excluded if they correspond to a contaminant introduced at an earlier point, for example, during collection of biological sample data.

Using the methods described above, even if an RNA read is not matched to a unique known RNA transcript, it may be possible to derive relative abundance data regarding those RNA transcripts using statistical methods, such as maximum likelihood estimation or Bayesian methods, and update the Results file. For other cases, some RNA reads may not be possible to be identified using statistical methods that can contribute to the Results file data. For example, human transcript expression can have enormous diversity and some transcript expressions can be too complex to map to a known transcript expression. Additionally, the RNA reads obtained from a patient can include reads that relate to items that may not be of interest for disease detection, treatment planning or drug discovery. For example, those RNA reads might come from a contaminant, bacteria source or a non-human source. On the other hand, some unmatched RNA reads, such as those too complex to be matched using the methods described above, can contain the gene patterns that may be useful for drug discovery or treatment analysis. As will be described below, the unmatched RNA reads can be identified using the described machine learning techniques and the Results file can be updated accordingly.

In step 103, these unmatchable RNA reads may be input to one or more machine learning classifiers, which output an indication of a gene or gene family that the unmatchable RNA read belongs to. The one or more machine learning classifiers may be used to predict the gene or gene family that the RNA read belongs to. By identification of the gene or gene family of the RNA read, an RNA transcript that the RNA read derives from may be determined. A machine learning classifier may be, for example, a computer program, module, system, function, or component. In some embodiments, a neural network (NN), a convolutional neural network (CNN), support vector machine (SVM), latent Dirichlet allocation (LDA), linear discriminant analysis, linear regression, random forest, or similar architectures can be used. In some embodiments, a plurality of machine learning algorithms, each trained to identify a different transcript expression can be used and run on each unmatched RNA transcript to classify the unmatched RNA reads. Additionally, matching an RNA read with a known transcript also determines the chromosomal gene from which the RNA read came from. So, disease and/or treatment analysis can be performed by analyzing expression level and/or gene level data. In addition to employing machine learning algorithms trained to classify human RNA expressions, machine learning algorithms trained to detect non-human or other categories of RNA expression, such as those trained to detect RNA expressions of viruses and bacteria, can be used.

A machine learning classifier accepts as input an encoding of the unmatchable RNA read and outputs a predicted classification, such as a gene or gene family of transcript expressions corresponding to the RNA read.

In another embodiment, a plurality of machine learning classifiers are used. Each of the machine learning classifiers outputs a prediction for a single class, such as a single gene or gene family. The prediction is a probability that the RNA read belongs to the class. A combiner may receive as input the outputs from the plurality of machine learning classifiers. The combiner may evaluate each of the predicted probabilities and assign the RNA read to the class with the highest output probability.

In step 104, some RNA reads (for example, unmatched RNA reads and/or a portion of matched RNA reads) may then be assembled into RNA transcripts from which they came from, in order to generate more disease or treatment related data. RNA assembly can provide a fine mapping of highly variable human genes. Assembling can also provide a way to identify unique RNA transcripts that might occur versus common RNA transcripts in one patient or in a population of patients. For example, an assembly of RNA reads in a patient population can reveal an RNA transcript that happens with high frequency and an RNA transcript that happens uniquely in a subset of patients. However, assembling RNA reads into their originating RNA transcripts can be computationally taxing. The matching step 102, the labeling and quantification step 102a, excluding unimportant data step 102b and the matching with machine learning step 103 can substantially reduce the universe of RNA reads which go through the assembly process. In one embodiment, RNA reads that are correctly indexed to an RNA transcript in steps 102, 102a are not put through the assembly process because they are already identified to a corresponding RNA transcript. In an embodiment, only RNA reads that were not identified to an RNA transcript or gene through indexing are put through the assembly process. For example, in one embodiment, only RNA reads that were mapped to a gene or gene family by the machine learning classifiers in step 103 are put through the assembly process.

In one embodiment, the assembly process of the step 104 can be performed by repeating the walking of the De Bruijn graph and/or alignment assembly. In an embodiment, a new De Bruijn graph can be constructed from the reads that the machine learning algorithm of the step 103 collects and used as an RNA scaffold. A plurality of De Bruijn graphs may be built, each corresponding to a partially constructed RNA transcript. The De Bruijn graphs may be filled in with RNA reads, by inputting an RNA read and iterating over the graph to find the location of the match. Completed graphs may correspond to an RNA transcript, and the completed RNA transcripts may be assembled and quantified. Moreover, the assembled RNA transcripts may be used to update the relative abundance of RNA transcripts in the Results file.

In another embodiment, the strengths of connections between the nodes of the newly constructed De Bruijn graph can be measured, for example, in terms of the frequency of connections between nodes. The strength information can provide an additional means for assembling RNA reads. Furthermore, the output of the machine learning (ML) algorithms can be used to resolve previous ambiguities that prevented finding a match for unmatched RNA reads by the De Bruijn graph. The ML outputs in combination with walking the De Bruijn graph can be used to find a match for unmatched RNA reads.

Other assembly techniques, such as overlap method, exhaustive matching methods and/or other RNA read assembly methods can also be used. For example, in some exhausting matching approaches RNA reads may be compared in an all-against-all manner to identify overlapping sequences. RNA reads may then be stitched together at the points of overlap.

In an embodiment, the RNA reads that come from the same RNA transcript or gene or gene family may be grouped together. RNA reads in the same group may then be assembled into RNA transcripts by identifying sequence portions at their ends that overlap with the sequence portion on an end of another RNA read. Overlap may be determined by finding identical or highly similar sequences, where similarity may be determined by the number of matching nucleotides when the sequences are overlaid. The process of combining RNA reads at their overlap positions may continue, like piecing together a puzzle, until a plurality of RNA transcripts is generated. As a result, the identity and quantity of various RNA transcripts in the biological sample is determined. The identity and quantity amounts may include some artifacts from the high-throughput sequencing process and so may not exactly match the identity and quantity of RNA transcripts in the raw sample. However, the identity and quantity measurements of the RNA transcripts still provide a window into the cellular activity at the time the sample was taken. The set of RNA transcripts reconstructed from the sample in the above manner may be referred to as the RNA transcriptome. It may be referred to as a reconstructed RNA transcriptome since it was reconstructed from a list of RNA reads.

The described embodiments estimate RNA transcripts in as close to reality as possible. RNA expression is measured by sequencing the RNA and estimating how much of the sequence in the sample is present. In controlled environments, where RNA is synthesized or otherwise generated with known parameters, RNA expression levels can be measured with near certainty, but in living organisms, measuring true RNA expression levels may not be achievable. Using the described embodiments, where high read depths (maximizing the number of next generation sequencing reads in an RNA read file) are employed, one can be very confident that RNA expression level estimations are close to reality.

In another embodiment, the assembly step 104 is a pseudo-assembly where RNA reads are matched to RNA scaffolds. The scaffolds comprise structures that match the nucleotide sequences of an RNA transcript and may be filled in with RNA reads. When sufficient RNA reads are identified in a scaffold, then it is determined that a copy of the RNA transcript is present. Quantity may be determined by counting the number of copies of scaffolds that are completely or partially filled in. Scaffolds may be counted for quantification of the RNA transcript even if the scaffold is not completely filled in, since some mutations or sequencing errors may cause RNA reads to be missing.

In an embodiment, the scaffolding process may be repeated multiple times with different subsamples of the RNA reads to verify the count of RNA transcripts that is derived. In an embodiment, a series of iterations are performed until a stopping condition is reached. At each iteration, a sample of the RNA reads is taken, which may be random or pseudo-random. The sampled RNA reads are matched to RNA scaffolds as described above and a quantification of the RNA transcripts performed. After the iterations are performed, the distribution of the quantities of RNA transcripts over the different iterations may be analyzed, such as by likelihood statistics, expectation maximization, or gradient descent. This process may verify the correctness of the derived quantities of the RNA transcripts. The analysis may be performed to determine that the relative quantities of RNA transcripts remains relatively constant no matter which sample was taken, which is indicative of a correct count.

In some embodiments, some of the RNA reads are assembled by using a stitching process and other of the RNA reads are pseudo-assembled using scaffolding. The resulting transcriptome comprising RNA transcripts may comprise on the order of 10,000 RNA transcripts or genes and corresponding quantities. As described above, the quantities may be expressed in terms of relative abundance of each identified RNA transcript. In some embodiments, relative abundances can be expressed in terms of normalized value, such as transcripts per million.

In step 105, samples may be taken from a plurality of patients and an RNA transcriptome data generated for each patient from a data file of their RNA reads created through high-throughput sequencing. Steps 101a-104 can be repeated for the plurality of patients and the Results file can accordingly be updated by the data from those patients. In step 105a, each patients' corresponding clinical status data (e.g., response to treatment data, indications of disease) can also be gathered and/or associated with a corresponding Results file. An indication may be recorded for each patient of whether they have or do not have a particular disease of interest. The indication of disease may be determined through medical tests, recording symptoms, or physician observations. A training set may be created from the RNA transcriptomes and corresponding data on whether the patient has or does not have the disease. In some embodiments, the disease of interest is a disease of the human immune system.

The term "disease" as used herein is defined to also include variation in treatment response (VITR). VITR may refer to a situation where patients with a disease react differently to the standard therapy for the disease than expected (usually more poorly than expected), for example having an incomplete response to the therapy so that the disease remains or where new disease features emerge as a result of the therapy, such as secondary inflammatory reactions. In an embodiment, samples may be taken from a plurality of patients and a results file for each patient from a data file of their RNA reads created through high-throughput sequencing, using methods described above. An indication may be recorded for each patient of whether they have or do not have a VITR. The indication of VITR may be determined through medical tests, recording symptoms, or physician observations.

A machine learning classifier may be trained on the training set, such that the machine learning classifier is trained to predict or identify gene patterns of interest in a patient population. Gene patterns of interest, for example, can include gene patterns in the Results files of the patients corresponding to failure to respond to a treatment. Those gene patterns can be candidates for further study for new treatments or new drug discoveries. In one embodiment, the machine learning classifier is trained to predict whether a patient has a disease or VITR, where the training adjusts one or more internal parameters of the machine learning classifier for making its prediction. After training, the machine learning classifier and its parameters may be analyzed to determine gene patterns of interest.

The machine learning classifier in the step 105 can be trained by the Results files and their associated patients' clinical status data. A training set may be created from the RNA transcriptomes of a patient population (the Results files) and corresponding patient clinical status data (e.g., whether the patient has or does not have the disease or VITR). A machine learning classifier, for example, a random forest, or support vector machine (SVM) may be trained on the training set, such that the machine learning classifier is trained to predict or identify gene patterns of interest from the Results files. In an embodiment, a machine learning classifier, for example, a random forest, or support vector machine (SVM) may be trained on the training set, such that the machine learning classifier is trained to predict or identify whether the patient has a disease or VITR from the Results file.

In step 106, analysis may be performed on the machine learning classifier to identify parameters that the classifier uses to classify disease or VITR. For example, parameters may correspond to particular RNA transcripts and corresponding genes, such as their quantity or presence in the transcriptome. These RNA transcripts and corresponding genes may be analyzed and determined to be predictive of existence of the disease or VITR.

In an embodiment, the machine learning classifier is a random forest that includes one or more trees that have split points at particular quantities of RNA transcripts. Analysis may be performed on the RNA transcripts selected by the random forest algorithm to identify RNA transcripts and corresponding genes that are predictive of the disease or VITR. In some embodiments, the RNA transcripts and corresponding genes that are predictive of the disease or VITR have an effect on the human immune system.

In step 107, optionally, methods and systems herein may be used for personalized medicine. A treatment may be tailored to a patient based on the patient's own RNA transcriptome. The machine learning classifier trained in step 105 may be applied to an RNA transcriptome of a new patient to predict whether the new patient has a disease/VITR or not. The collection of a sample and reconstruction of the RNA transcriptome (e.g., the Result file) for a new patient may be performed using, for example, steps 101 through 104. The output of the machine learning classifier is a prediction of disease/VITR or no disease/VITR.

In an embodiment, one or more trees of the random forest that are highly predictive may be selected and used to diagnose new patients. In order to diagnose a patient, a biological sample may be collected from the patient and RNA sequencing performed on the sample. The RNA transcriptome may then be reconstructed using the algorithmic methods described herein, such as steps 101 through 104. The RNA transcriptome may then be input to the one or more selected trees to determine a prediction of whether the patient has the disease or VITR of interest. In some embodiments, one tree is selected and used rather than multiple trees.

Once the patient has been diagnosed, a treatment may be applied to the patient. In some embodiments, the treatment may be a compound that was discovered to be effective by the method described above of analyzing the parameters of the machine learning classifier (step 106), where the same machine learning classifier or components of it are also used for diagnosis of patient by inputting a patient sample of RNA reads or transcriptome.

Figure 1B:
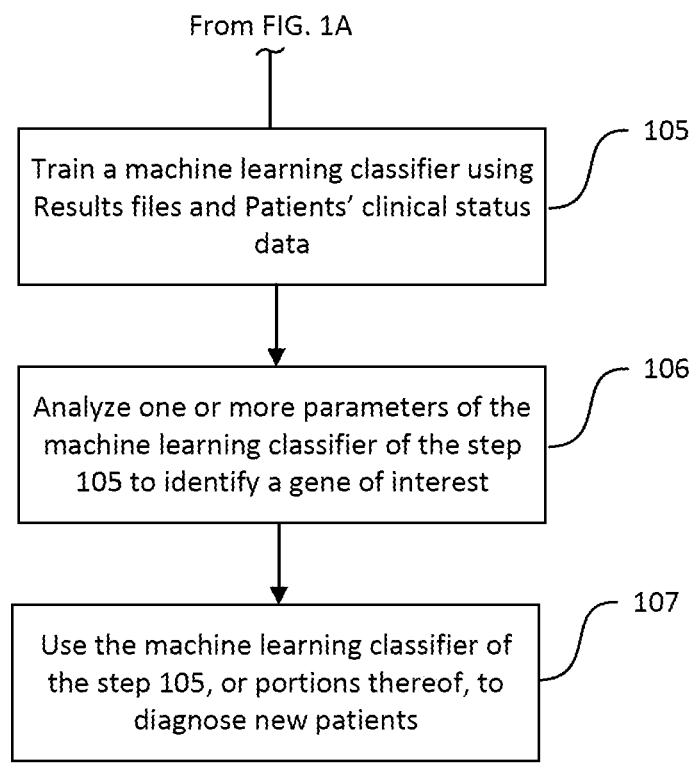
FIG. 1B illustrates another exemplary method for analysis of the RNA transcriptomes of a plurality of patients, which may be used in one embodiment.

FIG. 1B illustrates another exemplary computer-implemented method 110 for reconstruction of an RNA transcriptome and analysis of the RNA transcriptomes of a plurality of patients and associated disease data to determine one or more genes of interest in a disease or VITR. The collection of a biological sample and performing high-throughput RNA sequencing on a sample may be performed ahead of time to generate an unordered list of RNA reads. The RNA reads are the result of the high-throughput RNA sequencing. This unordered set of RNA reads may be provided in step 101b. The steps of building an index of known transcript expressions (step 101), matching a plurality of RNA reads to RNA transcripts (step 102), generating a Results files (step 102a), excluding data (step 102b), matching unmatched RNA reads from the prior step to a gene family by using one or more machine learning classifiers (step 103), assembling RNA reads into RNA transcripts (step 104), training a machine learning classifier using the Results files and patients' clinical status data (step 105), and analyzing one or more parameters of the machine learning classifier of the step 105 to identify a gene of interest (step 106) may be performed identically to method 100. Step 107 of method 100, where the classifier of the step 105, or a portion thereof, is used for diagnosis of a new patient is optional and so is not illustrated in FIG. 1B showing method 110.

Figure 1C:
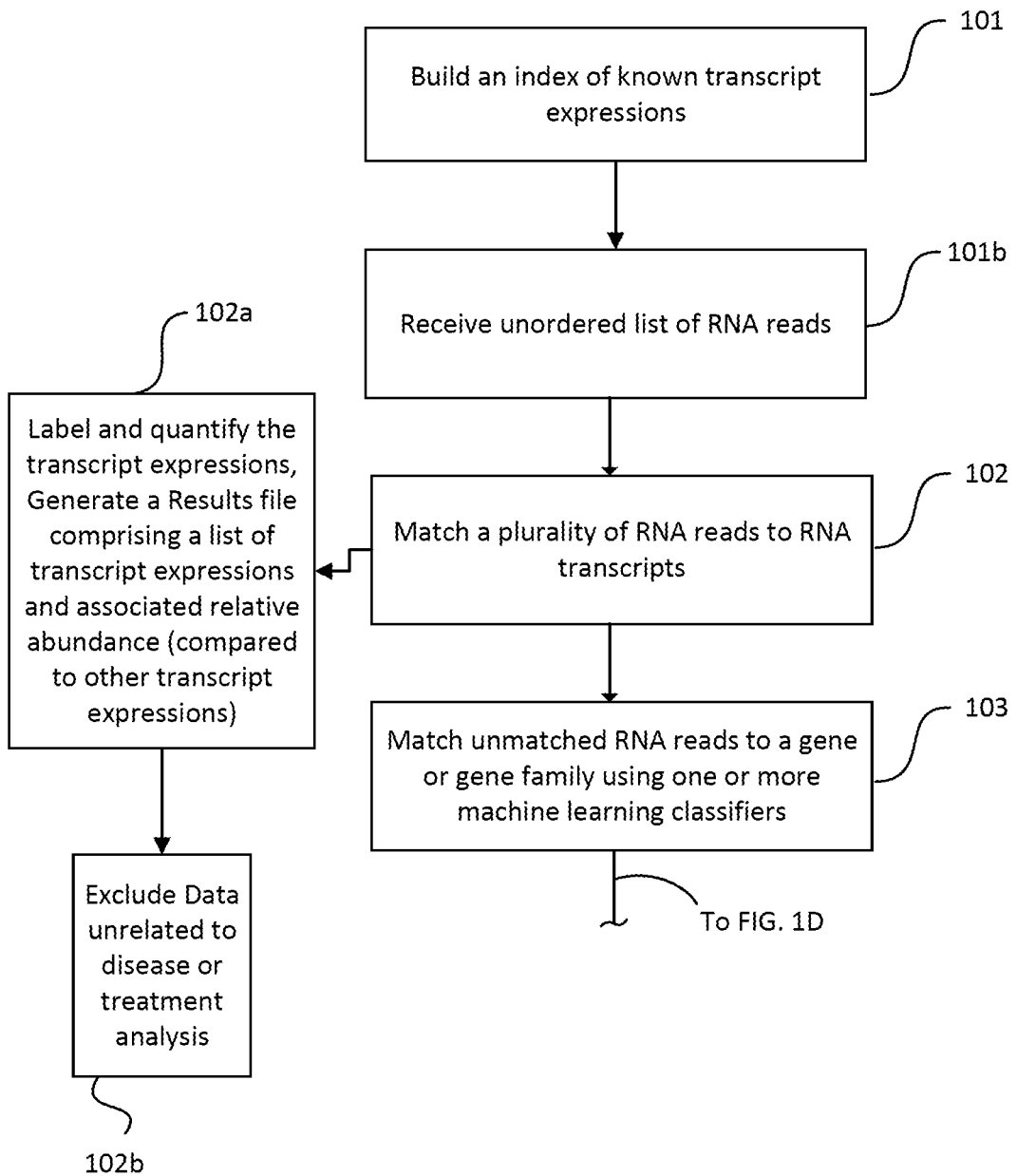
FIG. 1C illustrates an exemplary method for analysis of RNA transcriptomes of a plurality of patients, which may be used in one embodiment.
Figure 1D:
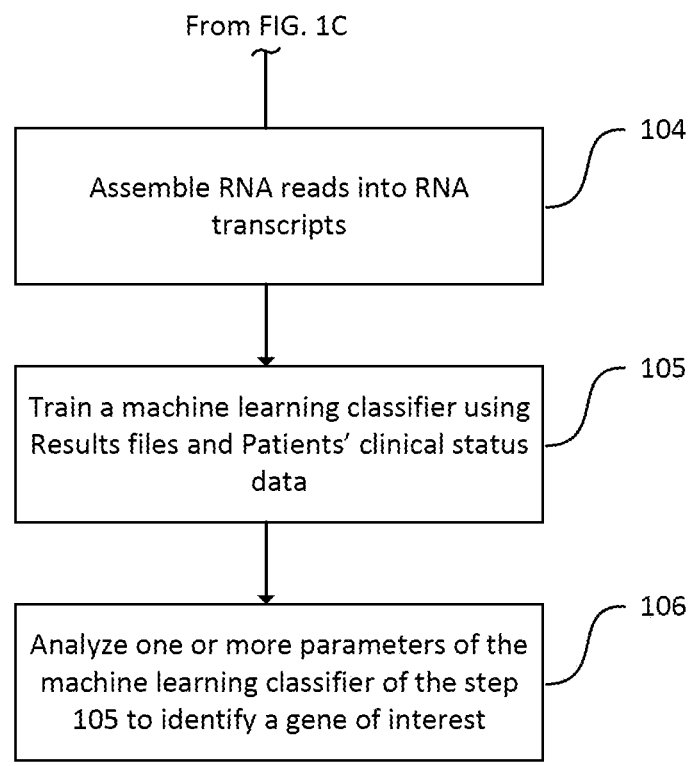
Figure 1E:
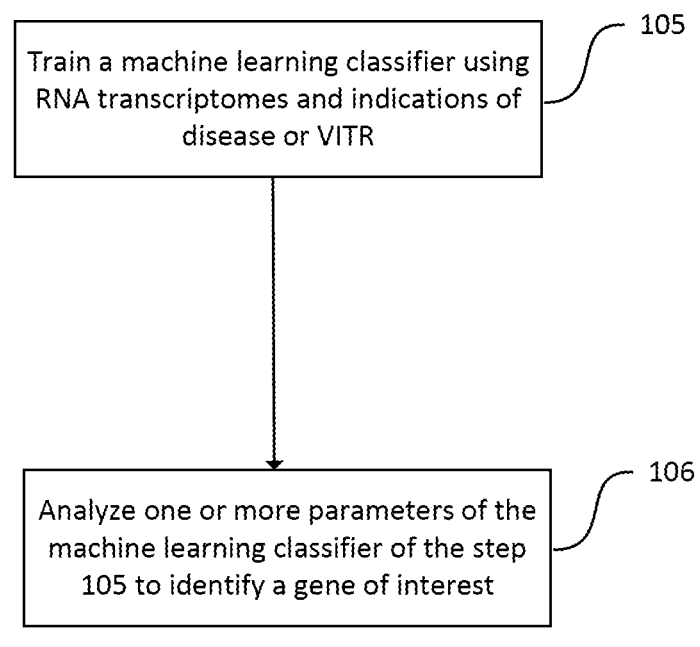

Moreover, the process of training the machine learning classifier of the step 105, using the Results files and patients' clinical status data (e.g., RNA transcriptomes and indications of disease or VITR) (step 105), and analyzing one or more parameters of the machine learning classifier of the step 105 to identify a gene of interest (step 106) may be performed separately from the other steps as shown in method 120 illustrated in FIG. 1C. In method 120, a set of RNA transcriptomes of a plurality of patients and an indication for each patient of whether the patient has a disease/VITR or not may be provided by any mechanism. Steps 105 and 106 may then be performed to identify a gene of interest.

Figure 2A:
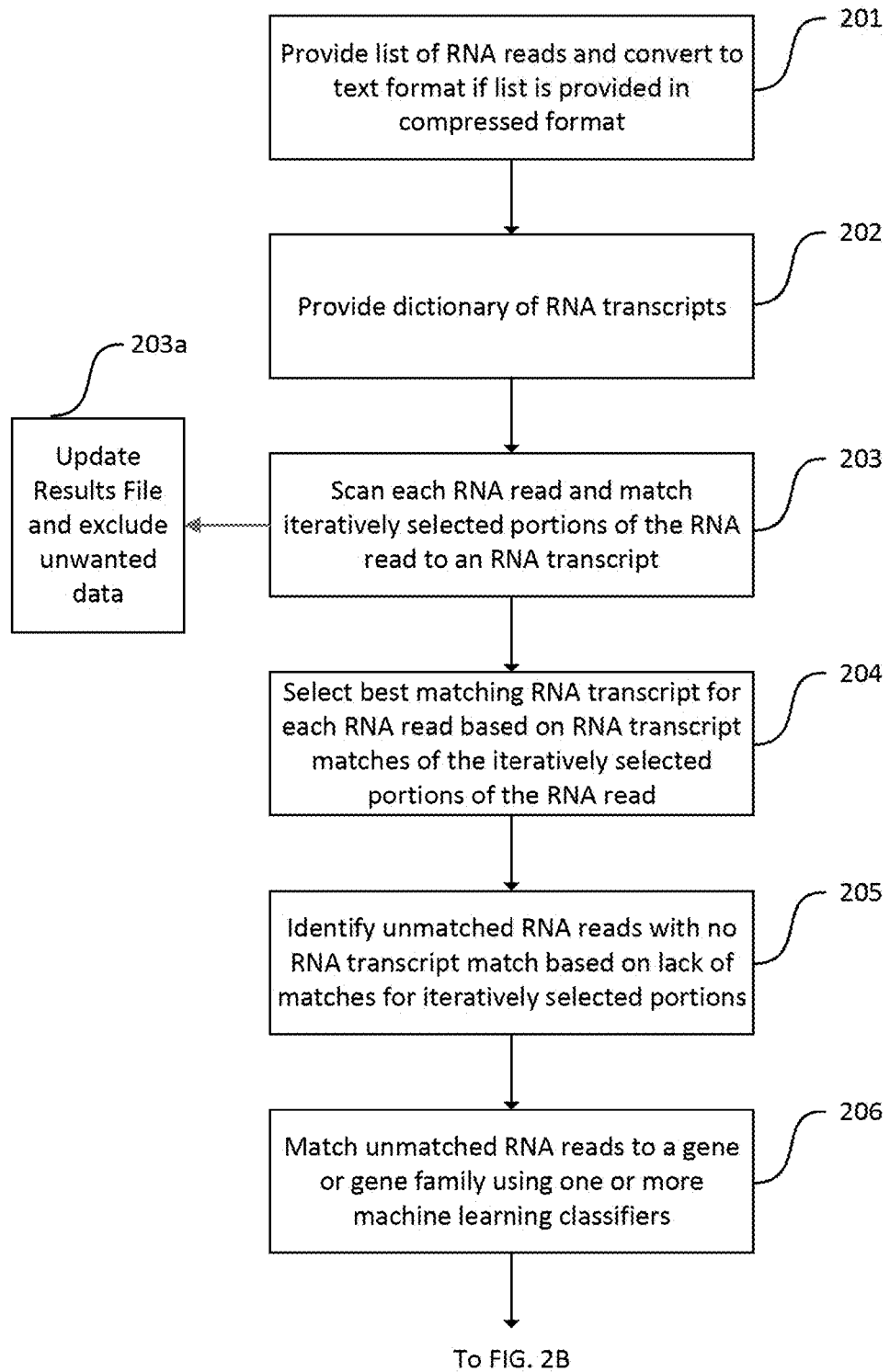
FIGS. 2A-B illustrates a more detailed view of an exemplary method for analysis of the RNA transcriptomes of a plurality of patients, which may be used in one embodiment.
Figure 2B:
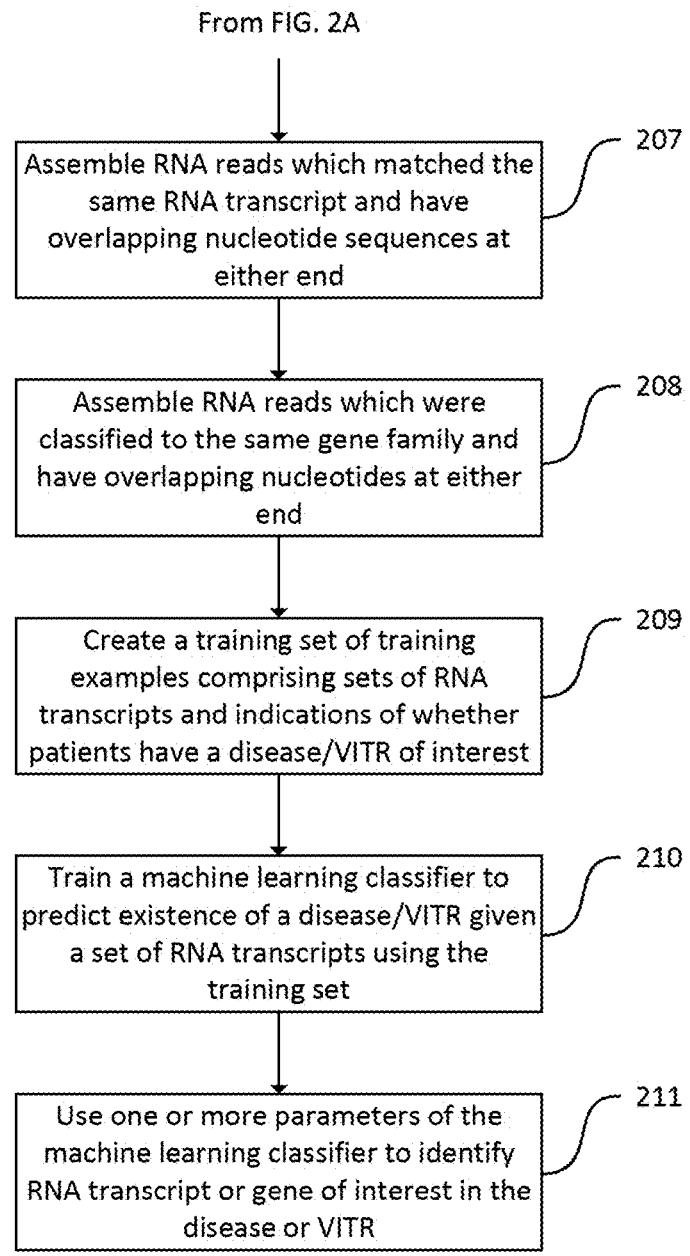

FIGS. 2A-B illustrate exemplary computer-implemented method 200, which is a more detailed implementation of methods 100-120. In step 201, a list of sequenced RNA reads from a sample of a patient is provided. The lengths of the sequenced RNA reads may be within a range, such as 50-250 nucleotides, 100-250 nucleotides, 100-300 nucleotides, or 100-400 nucleotides.

Optionally, the list of sequenced RNA reads may be compressed. For example, the list of sequenced RNA reads may be in a text format such as ASCII. Character encodings like ASCII often use one or more bytes per character. Since each nucleotide of sequenced RNA can only take one of four characters, the values of the nucleotides may be compressed by encoding them using 2 bits. Moreover, high-throughput sequencing may apply one or more computer-generated labels to RNA reads. Some or all of these computer-generated labels may be deleted from the file. In an embodiment, the list of sequenced RNA reads is compressed by removing one or more computer-generated labels and converting the list of sequenced RNA reads from a text format to a binary format. The compressed file may be stored in a memory local to a processor or on a remote server such as in the cloud.

When the list of sequenced RNA reads is about to be used, the compressed file may be downloaded to the local computer and then decompressed from the binary format to text format by reversing the process. The binary values are interpreted as characters according to the selected encoding. The corresponding characters may be sequentially output to create an uncompressed file.

In step 202, a dictionary of RNA transcripts may be provided. The dictionary of RNA transcripts may comprise a library of known RNA transcripts and associated information about the transcripts such as a corresponding gene or gene family. In an embodiment, a hash data structure may be created using selected portions of the RNA transcripts, where the hash entry indicates the corresponding full RNA transcript. This hash data structure allows fast lookup of RNA sequence portions to identify one or more matching full-length RNA transcripts. In an embodiment, a De Bruijn graph may generated from the dictionary of RNA transcripts, and RNA reads may be classified to a particular RNA transcript by walking through the De Bruijn graph.

In step 203, each RNA read may be scanned, such as from left to right, and iterative selection may be performed of a plurality of portions of each RNA read. The selected portions may be substantially shorter than the RNA read, such as 27-33 nucleotides, 25-35 nucleotides, 20-40 nucleotides, 10-50 nucleotides, or 20-50 nucleotides. In some embodiments, the selected portions may overlap each other. In other embodiments, the selected portions do not overlap. Iteration may be performed over each of the RNA reads, and each of the plurality of selected portions of the RNA read may be looked up in the dictionary of RNA transcripts. The look up identifies a set of candidate RNA transcripts that contain the corresponding selected portion.

In an embodiment, the look up of each portion of the plurality of portions of each RNA read in the dictionary of RNA transcripts is performed by hashing. For each particular portion of an RNA read, the portion may be input to a hash function to obtain a hash value, where the hash value may serve as an index that maps the portion to a cell of a hash data structure. The hash entry in the corresponding cell of the hash data structure may identify one or more RNA transcripts that contain the portion, which may comprise the set of candidate RNA transcripts, or may be empty if no RNA transcripts in the dictionary match the portion.

In step 204, for each of a first plurality of the RNA reads, a corresponding RNA transcript is determined based on the intersection of the set of candidate RNA transcripts of the associated RNA read. For example, if an RNA read has 4 portions that were iteratively selected, then each portion may be looked up in the RNA transcript dictionary to determine a set of candidate RNA transcripts containing the portion. An RNA transcript that appears in the set of candidate RNA transcripts for each selected portion may be selected as the corresponding RNA transcript of the RNA read. In some embodiments, errors in the RNA sequencing may lead nucleotides to be incorrectly transcribed. As a result, some portions of an RNA sequence may not match to the correct RNA transcript or may match an incorrect RNA transcript. In an embodiment, it is not required to identify an RNA transcript that matches all selected portions, but only that the RNA transcript match most of the selected portions or a plurality of the selected portions, such that it is the best match as compared to other candidate RNA transcripts. In an embodiment, the RNA transcript that matches the most of the iteratively selected portions of the read is chosen as the corresponding RNA transcript.

In another embodiment of the steps 203 and 204, each RNA read is walked along a De Bruijn graph to narrow down the identity of the RNA read (e.g., which known transcript is the RNA read from). For some RNA reads, an exact match with a known RNA transcript can be found by walking along the De Bruijn graph, and no ambiguity regarding its identity can be found. A corresponding counter associated with the transcript type can be incremented. For some RNA reads, the De Bruijn graph can narrow down the identity of the RNA reads between a group of potential RNA transcripts. This situation can occur because of the enormous diversity in the expressions of human genome (even within a single patient). For RNA reads whose identity can be narrowed down to two or more possibilities, a variety of methods can be used to establish a likelihood level of the RNA read belonging to various possible RNA transcript expressions. Examples include, maximum likelihood estimation (MLE) and Bayesian methods. In step 203a, these likelihood identity estimations, along with counters for positively identified RNA reads, can be used to generate a Results file for a patient, where the Results file contains a listing of RNA transcript expressions and their relative abundances compared to one another. Additionally, in step 203a, unwanted data can be excluded as described above.

For some RNA reads, the De Bruijn graph cannot output any identity. The unmatched RNA reads can be identified by using a plurality of machine learning models trained to detect various RNA transcripts. As described earlier, closer identification of the unmatched RNA reads (e.g., via assembly of those RNA reads into their originating RNA transcripts) can provide valuable insights for disease analysis and identification of potential gene patterns for new treatment or drug discovery.

In step 205, for each of a second plurality of the RNA reads, it may be determined that there is no corresponding RNA transcript in the dictionary of RNA transcripts that is a good match for the RNA read. For example, all or most of the selected portions of the RNA read may not match to a single RNA transcript or may match to no RNA transcripts in the dictionary. This may be due to the RNA read corresponding to a new RNA transcript that is not in the dictionary or due to the existence of a gene that encodes RNA transcripts with highly variable sequences.

In step 206, each of the second plurality of RNA reads may be matched to a predicted gene or gene family by using one or more machine learning classifiers, each trained to detect a gene or gene family of an RNA read. In an embodiment, each of the RNA reads in the second plurality of RNA reads is input into one or more machine learning classifiers (for example as an image tensor). Each of the one or more machine learning classifiers outputs a prediction of whether the RNA read is a member of a class, where the class may be a gene or gene family, and each of the one or more machine learning classifiers is trained to output its prediction for a different gene or gene family. For example, one of the machine learning classifiers may be trained just to determine whether an RNA transcript corresponds to the HLA gene family or not. A highest probability gene or family may then be assigned to each of the RNA reads in the second plurality of RNA reads based on the outputs of the machine learning classifiers. The gene or gene families may correspond to an RNA transcript or transcripts. Thus, in an embodiment, an RNA transcript may optionally be matched and assigned to the RNA reads in the second plurality of RNA reads based on the outputs of the one or more machine learning classifiers.

In one embodiment, a plurality of machine learning classifiers is used, where each classifier corresponds to a different gene or gene family and each classifier outputs a probability that the RNA read belongs to that gene or gene family. An RNA read is assigned to a gene or gene family by selecting the gene or gene family that was scored with the highest probability by the corresponding machine learning classifier.

In one embodiment, the plurality of machine learning classifiers each comprise a neural network. The plurality of machine learning classifiers may each comprise a convolutional neural network layer that accepts as input an encoding of an RNA read and outputs a first representation of the RNA read, a recurrent neural network layer that accepts as input the first representation of the RNA read and outputs a second representation of the RNA read, a feed forward neural network that accepts as input the second representation of the RNA read and outputs a third representation of the RNA read, and a classification neural network layer that accepts as input the third representation of the RNA read and outputs a value at one or more classification neural network layer nodes indicative of the probability that the input RNA read corresponds to an output gene family. In other embodiments, the one or more machine learning classifiers of the step 206 can be built using support vector machines, LDAs, and/or Markov chains.

In an embodiment, the one or more machine learning classifiers are trained to correctly predict the gene or gene family corresponding to an RNA read based on a training set. The training set may comprise labeled examples of RNA reads and their corresponding ground-truth gene or gene family. In some embodiments, the ground-truth gene or gene family may be represented by an RNA transcript. The machine learning classifiers may be trained to learn a model that maps an RNA read to a gene or gene family by iteratively inputting training examples, specifically the RNA read, and determining whether the output of the machine learning classifier matches the ground-truth label of the training example. At each iteration, the parameters of the machine learning classifier may be adjusted according to a learning algorithm to adjust the accuracy of the machine learning model so that its output is more likely to match the correct ground-truth label. When the machine learning classifiers are neural networks, the machine learning classifiers may be trained using backpropagation, such as by modifying one or more neural network node weights using gradient descent starting from the last neural network layer and progressing backwards through the neural network layers until the first neural network layer is reached.

In step 207, one or more of the RNA reads of the first plurality of RNA reads are assembled. In an embodiment, assembly may be performed by matching RNA reads to RNA scaffolds. Scaffolds correspond to RNA transcripts and may be filled in with matching RNA reads. In an embodiment, the scaffolds may comprise one or more De Bruijn graphs. When sufficient RNA reads are identified in a scaffold, then it is determined that a copy of the RNA transcript is present. Quantity may be determined by counting the number of copies of scaffolds that are completely or partially filled in. Scaffolds may be counted for quantification of the RNA transcript even if the scaffold is not completely filled in, since some mutations or sequencing errors may cause RNA reads to be missing.

In another embodiment, the assembly is performed by stitching. The stitching is performed based on one or more of the RNA reads mapping to the same RNA transcript and having an overlapping sequence of nucleotides at either end to create a first plurality of RNA transcripts. In an embodiment, the one or more RNA reads of the first plurality of RNA reads are grouped according to their RNA transcript or gene family. At that point, it would be known that these RNA reads come from the same RNA transcripts and should be reassembled. The RNA reads can then be combined by finding the overlapping sequences of nucleotides on their ends. In an embodiment, regions of overlap may be, for example, 20-30 nucleotides, 10-30 nucleotides, 10-40 nucleotides, 5-30 nucleotides, or other lengths of nucleotides.

In some embodiments, only a portion of the first plurality of RNA reads, that present potential for new treatments or drug discovery, are assembled. For the first plurality of RNA reads, which have gone through walking of the De Bruijn graph and quantification process of the step 203*a*, there is a high degree of confidence in their identity. However, some RNA reads may still be chosen to be assembled into their complete RNA transcripts if they are estimated or expected to provide more insight and data into understanding disease and/or treatment, which may correlate to them.

In another embodiment of the assembly process of the step 207, the RNA assembly can include using a De Bruijn graph and alignment assembly. For example, a new De Bruijn graph can be generated based on the reads collected by the machine learning algorithms of the step 206. The strength of connections between the De Bruijn graph nodes can be measured. This can include how frequently nodes are connected. For example, the frequency of ACGTG node in the De Bruijn graph connecting to CGTGT versus CGTGA can be measured. Typically, these strengths are skewed. For example, the node ACGTG may connect to the node CGTGT, some high number (e.g., 42 times), while the node ACGTG may connect to the node CGTGA, some relatively low number (e.g., 1 time). Therefore, the underlying gene is ACGTGT, and that ACGTGA can be deemed a transcription error or machine reading error. In this manner, the De Bruijn graph can act as a scaffold, upon which the underlying reads of the machine learning classifier of the step 206 can be laid to gain insight about the underlying gene. For example, all the reads where the nodes ACGTG connect to the nodes CGTGT can be followed to reach a consensus regarding the identity of the underlying gene.

In step 208, the process of step 207 is performed for the RNA reads that were mapped based on the machine learning classification. One or more RNA reads of the second plurality of RNA reads are assembled or stitched together. The stitching is performed based on one or more of the RNA reads mapping to the same gene or gene family and having an overlapping sequence of nucleotides at either end to create a second plurality of RNA transcripts. In an embodiment, the one or more RNA reads of the second plurality of RNA reads are grouped according to their RNA transcript or gene or gene family. At that point, it would be known that these RNA reads come from the same RNA transcripts and should be reassembled. The RNA reads can then be combined by finding the overlapping sequences of nucleotides on their ends. In an embodiment, regions of overlap may be, for example, 20-30 nucleotides, 10-30 nucleotides, 10-40 nucleotides, 5-30 nucleotides, or other lengths of nucleotides.

The RNA reads that were mapped based on the machine learning can also use the De Bruijn and alignment assembly, as described herein.

In step 209, a training set may be created for training a machine learning classifier to diagnose a disease or VITR based on a plurality of RNA transcripts. The training set may include the first plurality of RNA transcripts, the second plurality of RNA transcripts, an indication of whether patient has a disease/VITR of interest, and a third plurality of RNA transcripts for a plurality of patients and an indication for each of the plurality of patients of whether the patient has the disease or VITR. The training set can also include Results file data having relative abundance data of each RNA transcripts as well as RNA transcripts identified and annotated through the processes described above.

In step 210, a disease prediction machine learning classifier may be trained, based on the training set, to predict the existence of the disease or VITR based on an input set of RNA transcripts.

In step 211, one or more parameters of the disease prediction machine learning classifier may be used to identify at least one RNA transcript of interest or gene or gene family of interest in the disease or VITR.

In an embodiment, the disease prediction machine learning classifier comprises a random forest of random forest trees, wherein each of the random forest trees includes one or more split points. Moreover, the one or more parameters of the disease prediction machine learning classifier that identifies at least one RNA transcript of interest or gene of interest in the disease or VITR may comprise a split point of one of the trees.

More specifically, in an embodiment, the disease prediction machine learning classifier comprises a random forest and the random forest is generated by the following method. First, a sample of training examples is selected from the training set. The sampling process may be random or pseudorandom. Second, a random forest tree may be generated. A tree start node may be created. For each terminal node of the random forest tree, a subset of features of interest may be selected. Each feature of interest is an RNA transcript or gene family. A split point is then selected among the subset of features of interest in order to maximize information gain, which may be measured by reduction in entropy. That is, splitting the training examples at the split point should increase the information gain among the two split portions, and reduce entropy, with respect to the disease/ VITR outcome as compared to the unsplit group. As an alternative to information gain, the split point may be chosen by using the Gini index. Gini index is a measure of variance among samples and decreasing the Gini index increases classification quality. The use of the Gini index allows selection of a split point to increase classification quality of the tree and reduce the amount of error.

A split point in the tree may correspond to a quantity of an RNA transcript or gene family feature of interest. That is, training examples are grouped based on whether their RNA transcriptome includes the specified quantity of the RNA transcript or gene family or not. At least two daughter nodes of the terminal node are created. In an embodiment, the training examples that meet the threshold of the split point assigned to a first daughter node and the training examples that do not meet the threshold of the split point assigned to a second daughter node. The process of splitting terminal nodes is repeated until a stopping condition is reached.

When the disease prediction machine learning classifier is a random forest, then the one or more parameters of the disease prediction machine learning classifier that identify at least one RNA transcript of interest or gene of interest in the disease or VITR may comprise a split point of one of the random forest trees. For example, the split point may define a quantity of an RNA transcript or gene family that is highly predictive of the disease or VITR and thereby show that the RNA transcript or gene family is predictive of the disease or VITR.

In another embodiment, a parameter of a random forest classifier that identifies an RNA transcript or gene of interest may be found by identifying characteristics of split points across multiple trees. For example, a characteristic that may be used is for identifying genes of interest is how often a feature is used as a split point in a random forest tree or the amount of information gain or amount of decrease in the Gini index. In an embodiment, genes of interest are identified by the number of times that the gene appears as a feature split point in the trees of the random forest. For example, a gene that appears as a split point the most, compared to other genes, may be selected as a gene of interest.

Figure 3A:
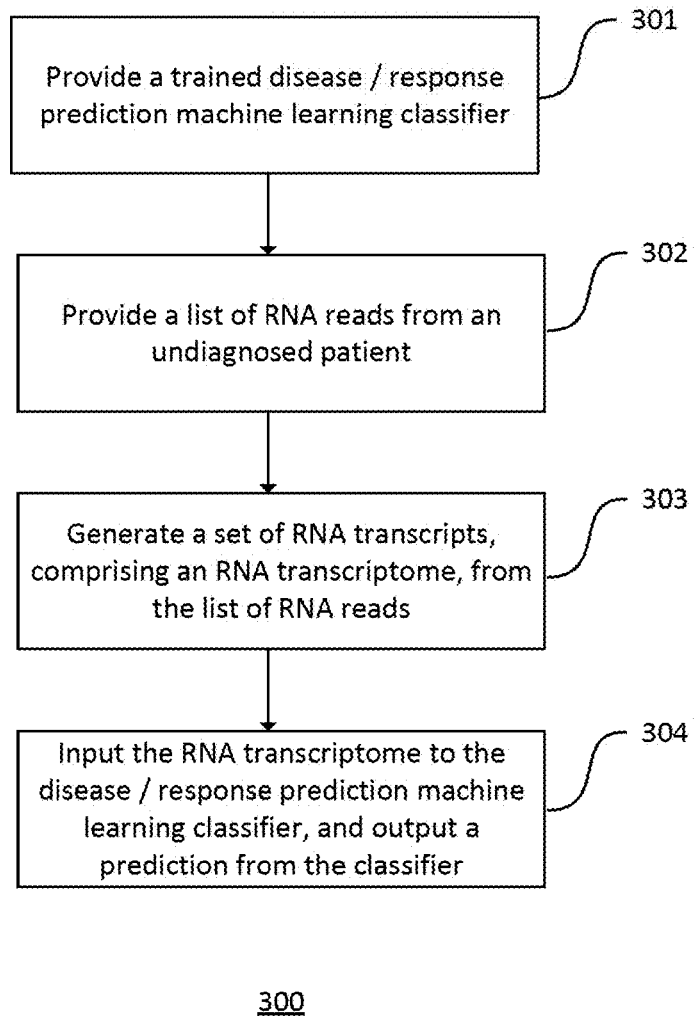
FIG. 3A illustrates an exemplary method that may be used for diagnosis of a patient, which may be used in one embodiment.

FIG. 3A illustrates an exemplary computer-implemented method 300 for diagnosis of a patient. The method 300 may use a disease prediction machine learning classifier trained using the methods 100, 110, 120, 200, or other methods and use the classifier to predict a diagnosis of a new patient. In step 301, a disease prediction machine learning classifier is provided, where the classifier has been trained to output predictions of whether a patient has a specified disease or VITR. In one embodiment, the disease prediction machine learning classifier is a random forest classifier. In step 302, a list of sequenced RNA reads from a sample of an undiagnosed patient is provided. In step 303, a set of RNA transcripts, comprising an RNA transcriptome, is generated from the RNA reads of the undiagnosed patient. The RNA transcriptome may be generated, for example, using steps 201 through 208. In step 304, the set of RNA transcripts, comprising the RNA transcriptome, are input into the disease prediction machine learning classifier and the classifier outputs a prediction of whether the undiagnosed patient has the specified disease or VITR. In an embodiment, the classifier outputs a prediction of whether the undiagnosed patient would benefit from a treatment that reduces or enhances the activity of the RNA transcript of interest or gene of interest of the disease or VITR.

Figure 3B:
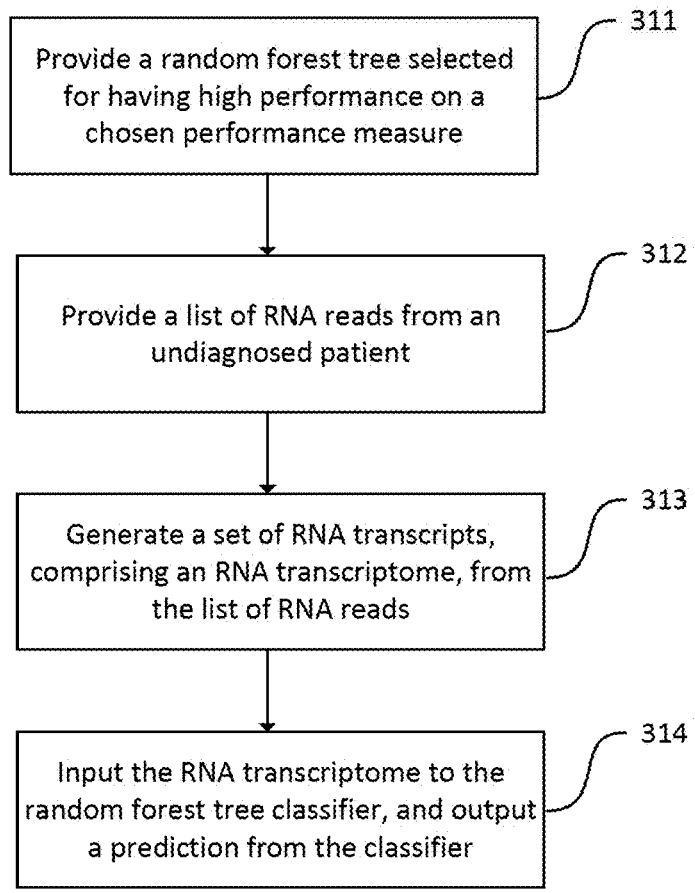
FIG. 3B illustrates another exemplary method that may be used for diagnosis of a patient, which may be used in one embodiment.

FIG. 3B illustrates an exemplary computer-implemented method 310 for diagnosis of a patient. The method 310 may use a random forest tree generated using methods 100, 110, 120, 200, or other methods and use the random forest tree to predict a diagnosis of a new patient. A random forest classifier is provided, where the random forest classifier was trained to output predictions of whether a patient has a specified disease or VITR. A single random forest tree of the random forest classifier is selected for having high classification performance in predicting presence of the disease or VITR, where the high classification performance may be measured by accuracy, recall, false positives, false negatives, or some combination of these measures or other measures. In step 311, the selected single random forest tree is provided. In step 312, a list of sequenced RNA reads from a sample of an undiagnosed patient is provided. In step 313, a set of RNA transcripts, comprising an RNA transcriptome, is generated from the RNA reads of the undiagnosed patient. The RNA transcriptome may be generated, for example, using steps 201 through 208. In step 314, the set of RNA transcripts of the undiagnosed patient is input into the selected random forest tree to diagnose whether the undiagnosed patient has the disease or VITR. In an embodiment, the classifier outputs a prediction of whether the undiagnosed patient would benefit from a treatment that reduces or enhances the activity of the RNA transcript of interest or gene of interest of the disease or VITR.

Figure 4:
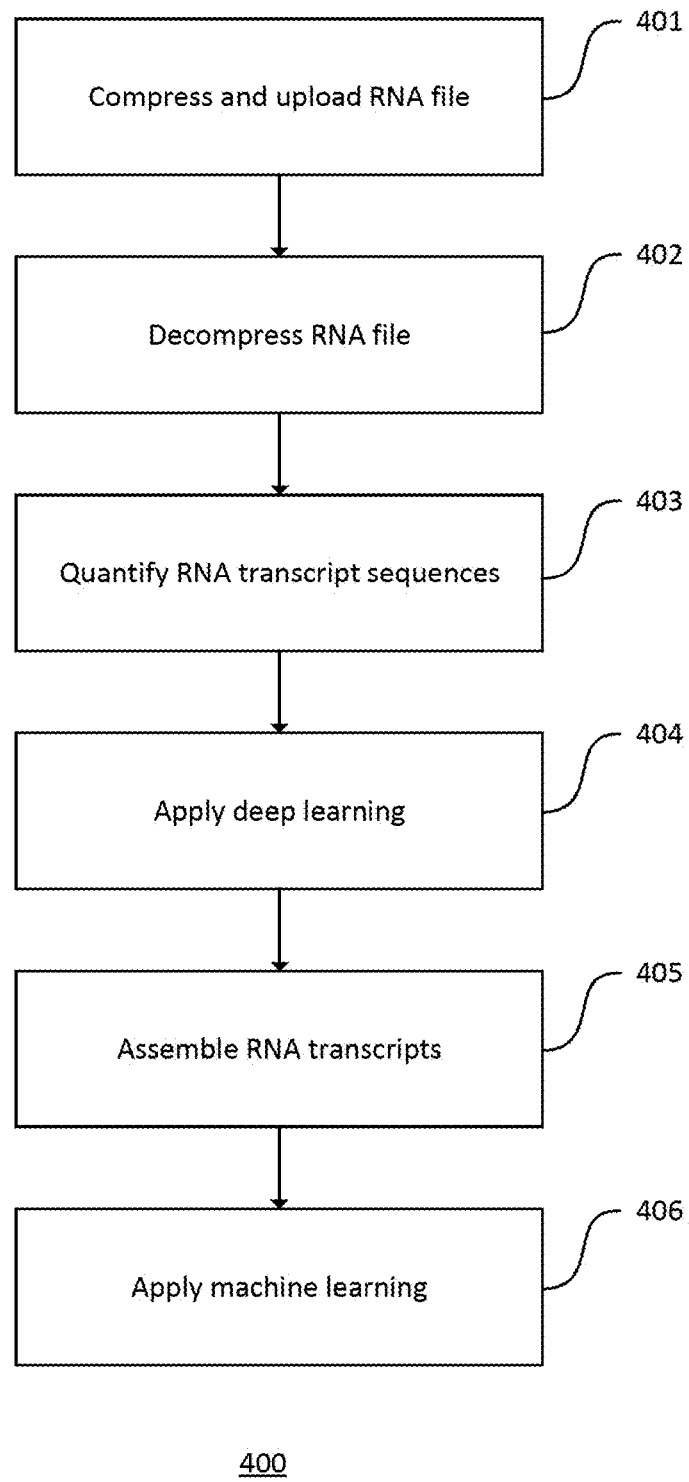
FIG. 4 illustrates a set of high-level steps that may be performed for analysis of a transcriptome and identifying one or more genes of interest in a disease or treatment response, which may be used in one embodiment.

FIG. 4 illustrates an exemplary set of high-level steps 400 that may be performed by methods 100, 110, 120, 200, 300, 310, and other methods. Step 401 comprises compression and upload. Step 402 comprises decompression. Step 403 comprises quantification. Step 404 comprises deep learning. Step 405 comprises assembly. Step 406 comprises machine learning.

Each of these steps may be used as part of an RNA sequencing, transcriptome reconstruction, and drug discovery process and will be described in turn. RNA provides a dynamic record of the activities of a cell at any point in time. The RNA transcripts present in a cell can provide insights into what decisions, so to speak, a cell was making just before it was removed from the body. The presence of RNA transcripts can provide insight into the state of the patient's immune system. A problem in the art is that the data returned by high-throughput RNA sequencing is large, unorganized, and difficult to interpret without computerized methods of interpretation.

I. RNA Reads

Figure 5:
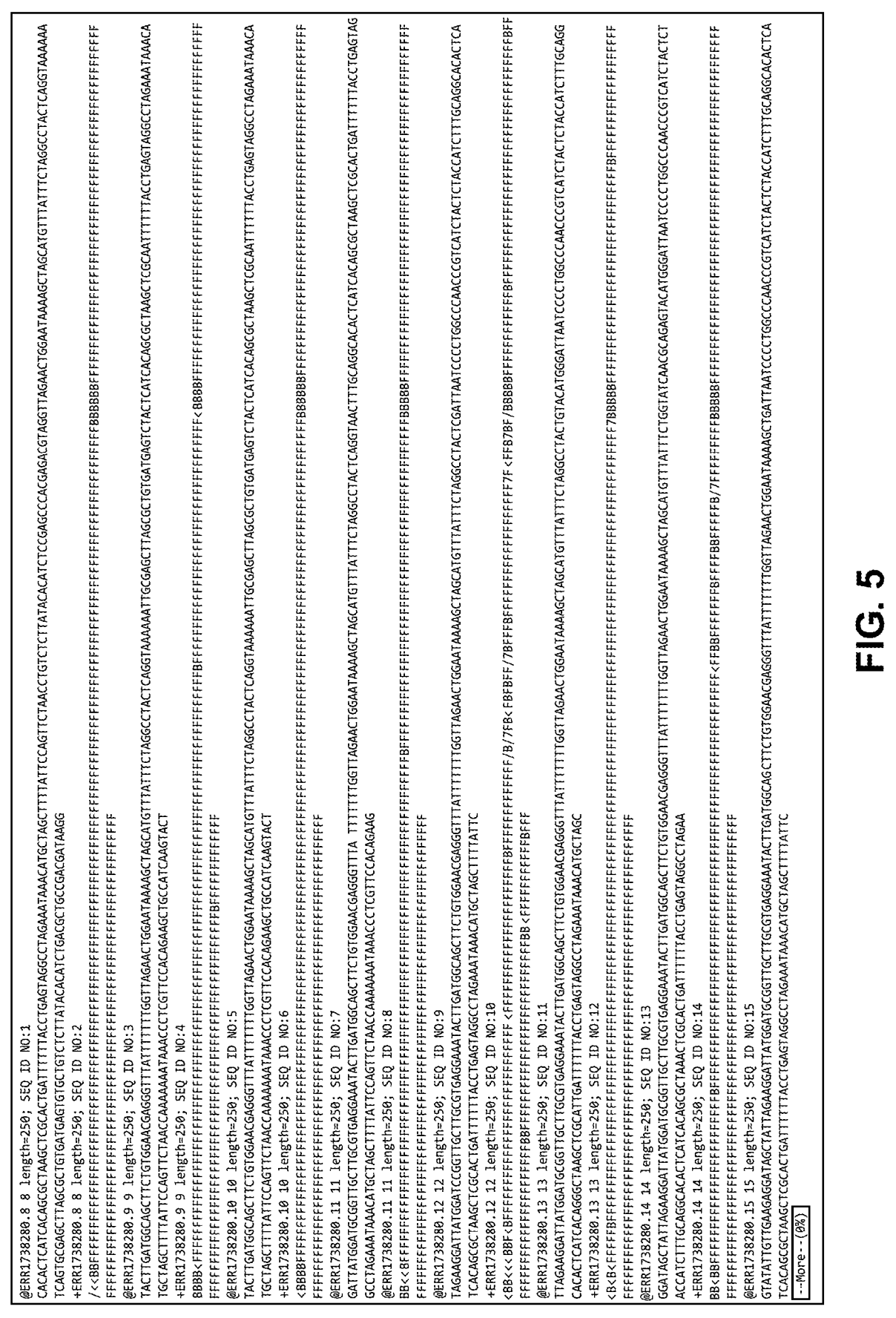

FIG. 5 illustrates an exemplary list of RNA reads output by the high-throughput sequencing process. The RNA reads are unordered and RNA reads from the same RNA transcript may appear anywhere else in the file. Each RNA read comprises a sequential string of characters, where each character represents a nucleotide. In this example, the RNA reads are 250 nucleotides long, but they may also be of other lengths. The RNA reads in this example also have a computer-assigned identifier.

The nucleotides in RNA are typically represented by the letters G, U, A, and C for Guanine, Uracil, Adenine, and Cytosine. In this example, the RNA sequences were reverse transcribed to cDNA (complementary DNA) and the cDNA was sequenced. This technique may be used because DNA sequencing technology is, in some aspects, more mature, so that sequencing the cDNA is easier than sequencing the RNA directly and, in any case, identifies the RNA sequence. The cDNA nucleotides are represented by the letters G, T, A, and C for Guanine, Thymine, Adenine, and Cytosine.

In an exemplary file of RNA reads collected from a biological sample may have hundreds of millions of reads. The file in .fasta format may have a file size of one hundred gigabytes or more. Therefore, it may be desirable to compress the file for storage.

II. Compression and Upload

The file of RNA reads is stored on a local computer system after the high-throughput sequencing is performed. Transferring the file to other computers is desirable, but it is difficult to transfer in uncompressed form. Therefore, a compression step may be performed to reduce the size of the file for transfer and storage.

Figure 6:
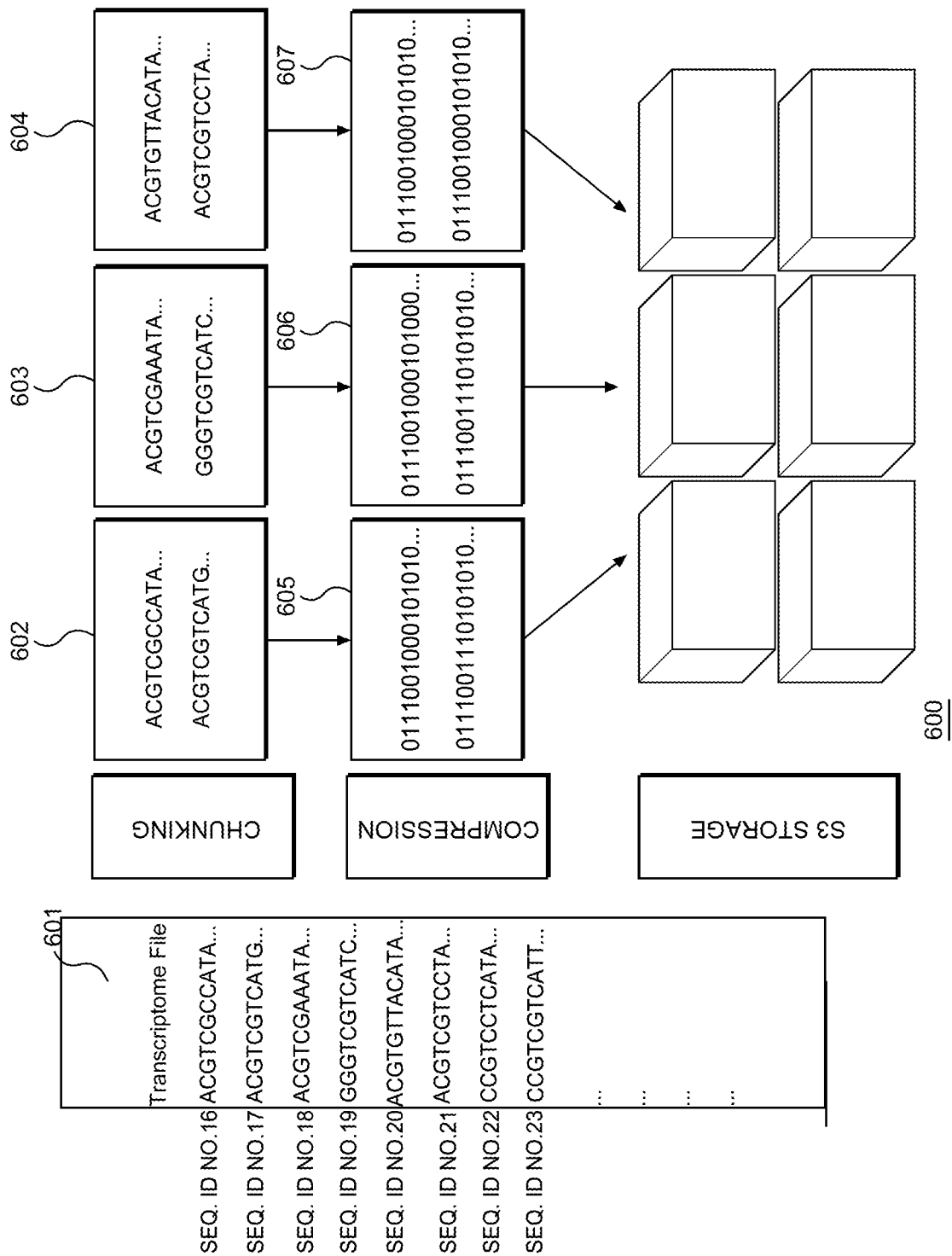
FIG. 6 illustrates an exemplary compression, upload, and storage process, which may be used in one embodiment.

FIG. 6 illustrates a compression, upload, and storage process 600. A raw transcriptome file 601 is provided that includes the unordered list of RNA reads that is output by a high-throughput sequencing machine. The single file is split into a plurality of smaller files 602-604 through a process called chunking. Unnecessary computer-generated labels from the high-throughput sequencing are removed from the files by deletion. The nucleotide text of each sequence is then compressed from the text format, such as ASCII, into a binary format. Text formats may use multiple bytes per character, while a binary format can represent each nucleotide using only 2 bits. An encoding is selected so that each nucleotide corresponds to a particular 2-bit value. The plurality of smaller files are processed to translate each nucleotide character into the corresponding 2-bit value. The files may be processed in parallel, though each file may be parsed sequentially from beginning to end. The resulting set of binary files 605-607 are then uploaded to a remote server, such as one or more servers in the cloud.

III. Decompression

Decompression of the smaller files may be performed by performing the reverse operation of the compression process. Each of the smaller files may be processed by iterating over the 2-bit values in the file. Each 2-bit value is translated to the corresponding nucleotide character based on the selected character encoding. The files may be processed in parallel to each other for decompression. Optionally, the smaller files may be concatenated together to create a single raw transcriptome file.

IV. Quantification

In one embodiment, to quantify RNA transcript sequences, the processing computer system hashes the RNA reads and looks them up in a dictionary of known RNA transcripts.

In one embodiment, a full RNA read may be hashed to the dictionary of known RNA transcripts. However, this approach has the disadvantage that the full RNA read may have mutations or errors from the high-throughput sequencing process and therefore may not correctly match with the corresponding RNA transcript.

In another embodiment, the full RNA read may be compared to find the closest RNA transcript by algorithms such as edit distance or max-flow min-cut.

Figure 7:
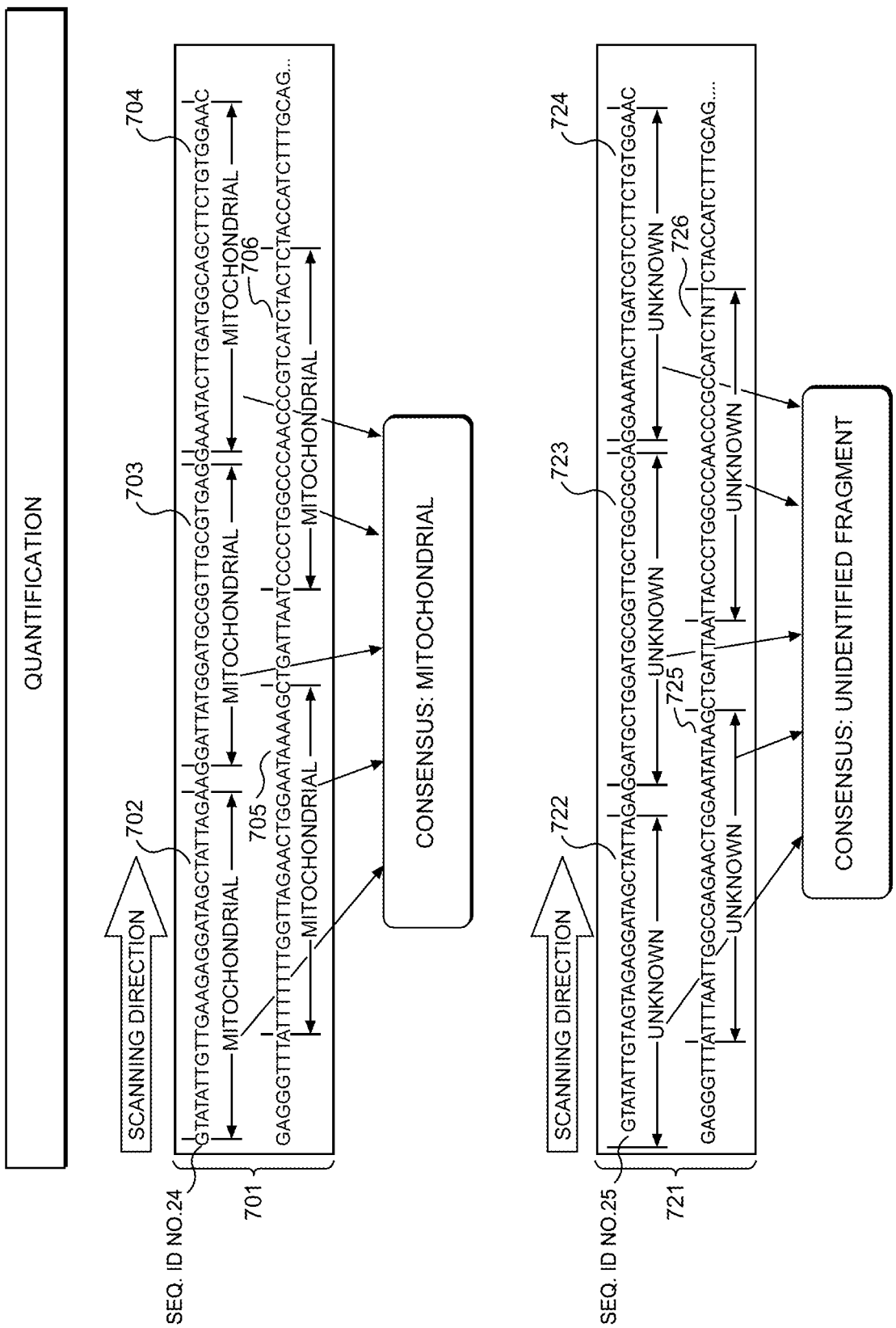
FIG. 7 illustrates an exemplary quantification step, which may be used in one embodiment.

FIG. 7 illustrates an embodiment where quantification is performed by selecting subsequences of the RNA read and hashing the subsequences to the dictionary of RNA transcripts to find a match. An RNA transcript that matches many of the subsequences may be selected by the processing computer system as the best match. In some embodiments, an RNA transcript in the dictionary that matches the most of the selected subsequences of the RNA read, as compared to other RNA transcripts, is selected as the best matching RNA transcript of the RNA read.

In an embodiment, an RNA read 701 is scanned left to right. Sub-portions 702, 703, 704, 705, and 706 are selected during the iterative left-to-right scan. These sub-portions are hashed to a dictionary of RNA transcripts to identify a matching RNA transcript sequence. Each of the sub-portions may map to one or more RNA transcripts. The matching RNA transcript of the entire RNA read may be selected based on the intersection of matches of each of the sub-portions, which may be performed by selecting the RNA transcript that matches the most of the sub-portions, or in some embodiments, all of the sub-portions. A consensus is determined based on the matches of the sub-portions that the RNA read 701 corresponds to mitochondrial RNA. Further specificity in the type of RNA may be determined with additional matches of sub-portions. For example, a specific gene or gene family may be identified based on the sub-portion matches.

An RNA read 721 is scanned left to right. Sub-portions 722, 723, 724, 725, and 726 are selected during the iterative left-to-right scan. These sub-portions are hashed to the dictionary of RNA transcripts. However, the sub-portions do not match a known RNA transcript. Therefore, the RNA read 721 is determined to be unknown in the quantification phase.

In some embodiments, the left-to-right scan and matching of sub-portions to an RNA transcript, such as by hashing, is also used as the scaffolding step. Once the RNA read is matched to an RNA transcript, a corresponding portion of an RNA scaffold may be filled in. The result of analyzing and counting all of the RNA scaffolds may provide a count of the quantities of each RNA transcript.

Figure 8:
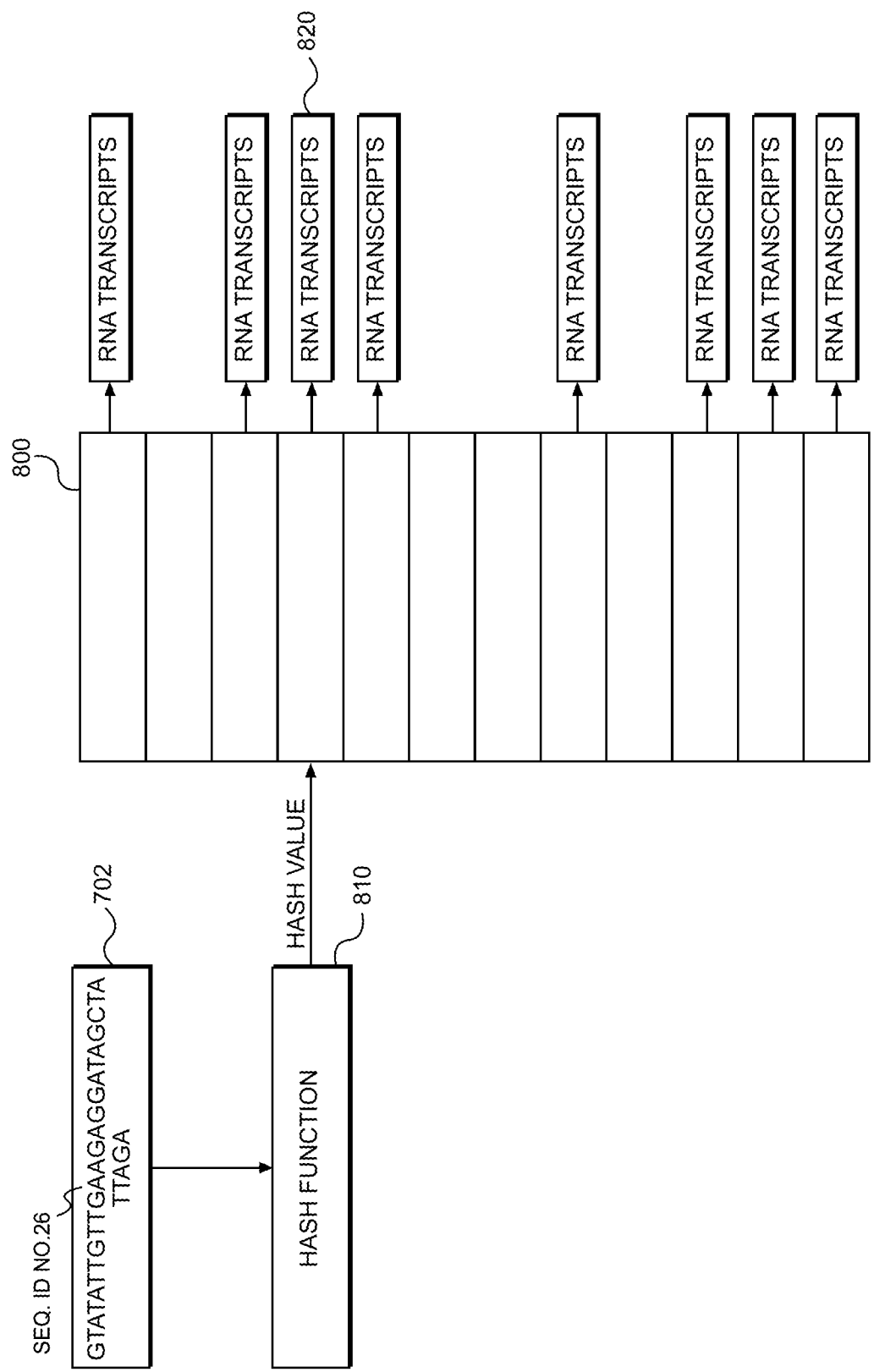
FIG. 8 illustrates an exemplary hashing process, which may be used in one embodiment.

FIG. 8 illustrates the hashing process described above. Sub-portion 702 is illustrated hashing into a hash table 800 that comprises part of the dictionary of RNA transcripts. The hash table 800 includes a plurality of entries that each correspond to a hash value. Each entry may contain a set of zero or more RNA transcripts, where the RNA transcripts contain a sub-sequence which hashes to the same hash value. Sub-portion 702 is input into a hash function 810, and a corresponding hash value is generated, whereupon the sub-portion 702 is hashed to the corresponding entry in the hash table. In this manner, the hash value acts as an index into the hash table 800. The corresponding entry of the hash table 800 includes a set of RNA transcripts 820 that include the matched sub-portion 702.

V. Deep Learning

The quantification step does not identify highly variant genes, which are highly variant between populations and individuals. Highly variant genes can generate RNA transcripts of many differing sequences. Moreover, the quantification does not identify unknown genes that are not in the RNA transcript dictionary.

Figure 9:
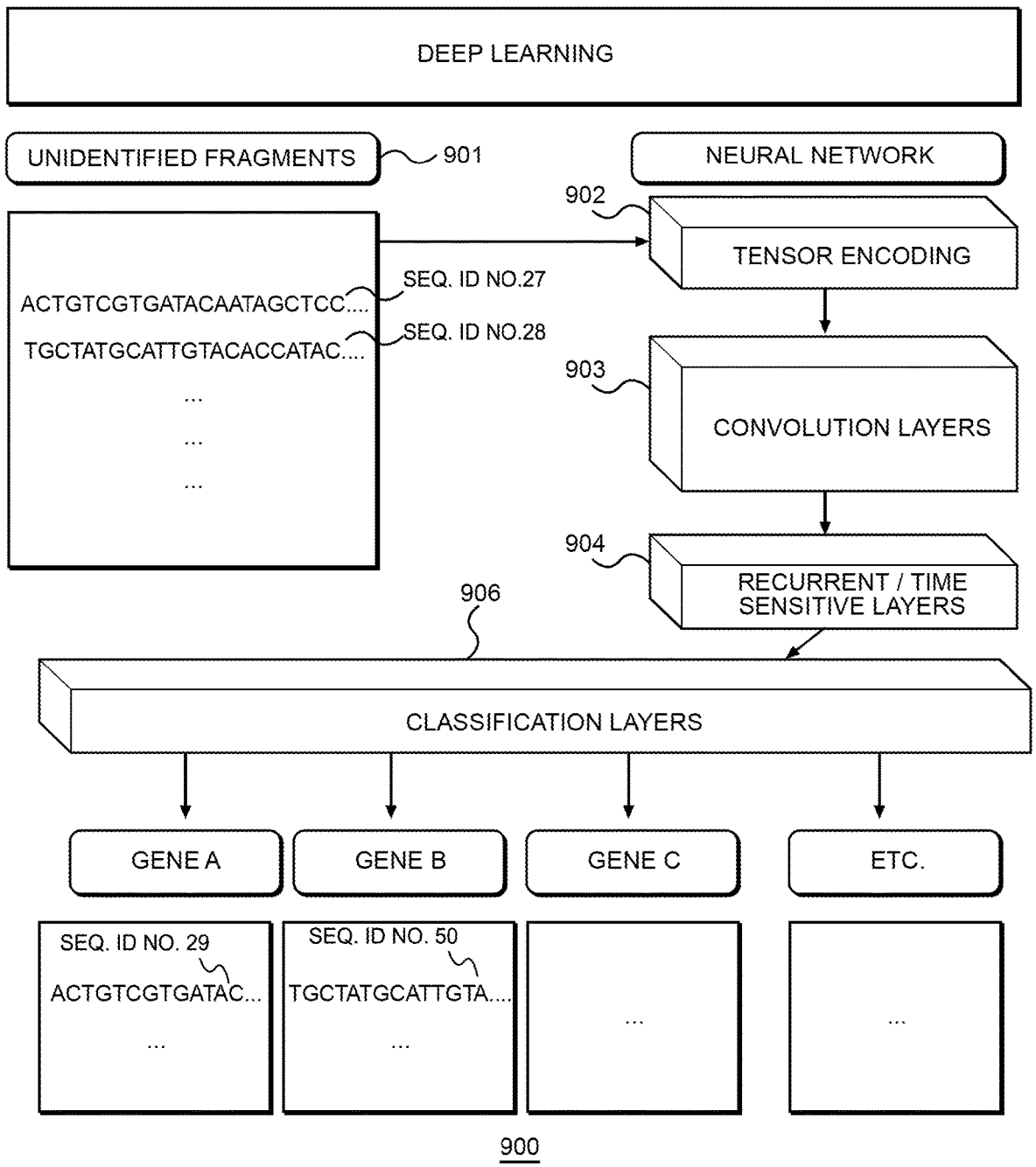
FIG. 9 illustrates an exemplary deep learning neural network, which may be used in one embodiment.

FIG. 9 illustrates an exemplary deep learning network 900 that may be used to identify variant genes. Moreover, the deep learning network may identify a gene family of unknown genes.

Neural networks may be comprised of a plurality of neural network nodes, where each node includes input values and calculates an activation function on the input values. The activation function may be a non-linear function computed on a weighted sum of the input values plus an optional constant. In some embodiments, the activation function is logistic, sigmoid, rectifier, or a hyperbolic tangent function. Neural network nodes may be connected to each other such that the output of one node is the input of another node. Moreover, neural network nodes may be organized into layers, each layer comprising one or more nodes.

In an embodiment, the RNA reads 901 that were not successfully identified in the quantification step are encoded into tensors. Tensors are matrices that may have any number of dimensions, such as 0, 1, 2, 3, or more. In an embodiment, each nucleotide may be encoded as a 1-hot array, where a single value is set to 1 and the remaining values are set to 0. The location of the 1 in the array is indicative of the nucleotide identity. These 1-hot arrays are then entries in a 1-dimensional array or tensor 902, which lists the 1-hot arrays in order of their sequence in the RNA read.

For example, in an embodiment, the sequence ACGTA may be represented by the following tensor:

[[1, 0, 0, 0],
[0, 1, 0, 0],
[0, 0, 1, 0],
[0, 0, 0, 1],
[1, 0, 0, 0]]

The tensor is input into a convolutional neural network (CNN) 903 comprising one or more convolutional neural network layers. A convolutional neural network layer includes one or more convolutional filters, also known as kernels, that operate on the outputs of the neural network layer that precede it and produce an output to be consumed by the neural network layer subsequent to it. A convolutional filter has a window in which it operates. The window is spatially local. A node of the preceding layer may be connected to a node in the current layer if the node of the preceding layer is within the window. If it is not within the window, then it is not connected. A convolutional neural network is one kind of locally connected neural network, which is a neural network where neural network nodes are connected to nodes of a preceding layer that are within a spatially local area. Moreover, a convolutional neural network is one kind of sparsely connected neural network, which is a neural network where most of the nodes of each hidden layer are connected to fewer than half of the nodes in the subsequent layer.

The output of the convolutional neural network is passed to a recurrent neural network 904 or other form of time sensitive layer. A recurrent neural network (RNN) 904 includes at least one back loop, where the output of at least one neural network node is input into a neural network node of a prior layer. The recurrent neural network 904 maintains state between iterations, such as in the form of a tensor. The state is updated at each iteration, and the state tensor is passed as input to the recurrent neural network 904 at the new iteration.

In some embodiments, the recurrent neural network is a long short-term (LSTM) memory neural network. In some embodiments, the recurrent neural network is a bi-directional LSTM neural network.

A feed forward neural network may accept the output of the recurrent or time sensitive layer. The feed forward neural network does not include back loops and may be densely connected, meaning that most of the neural network nodes in each layer are connected to most of the neural network nodes in the subsequent layer. In some embodiments, the feed forward neural network is a fully-connected neural network, where each of the neural network nodes is connected to each neural network node in the subsequent layer. The feed forward neural network outputs data that is consumed by the classification layer.

The classification layer 906 may comprise a layer of output nodes, where each output node corresponds to an output prediction, such as an RNA transcript, gene, or gene family. Each output node may have an output value corresponding to a probability that the output prediction is correct.

In some embodiments, a plurality of deep learning neural networks 900 are used, where each of the plurality of deep learning neural networks 900 is trained to make a prediction for a different RNA transcript, gene, or gene family. For example, one deep learning neural network may output a probability that an RNA read corresponds to the HLA gene family. From the outputs of the plurality of deep learning neural networks 900, the output having the highest probability may be selected as the correct classification for the RNA read.

In some embodiments, one or more of the deep learning neural networks produces only a binary result, namely a probability that the RNA read belongs to a given gene or gene family. In other embodiments, one or more of the deep learning neural networks may produce a multi-class result, and produce a probability that the RNA read is in one of a plurality of classes. For example, the multi-class deep learning neural network may classify an RNA read into a gene sub-family.

Figure 10:
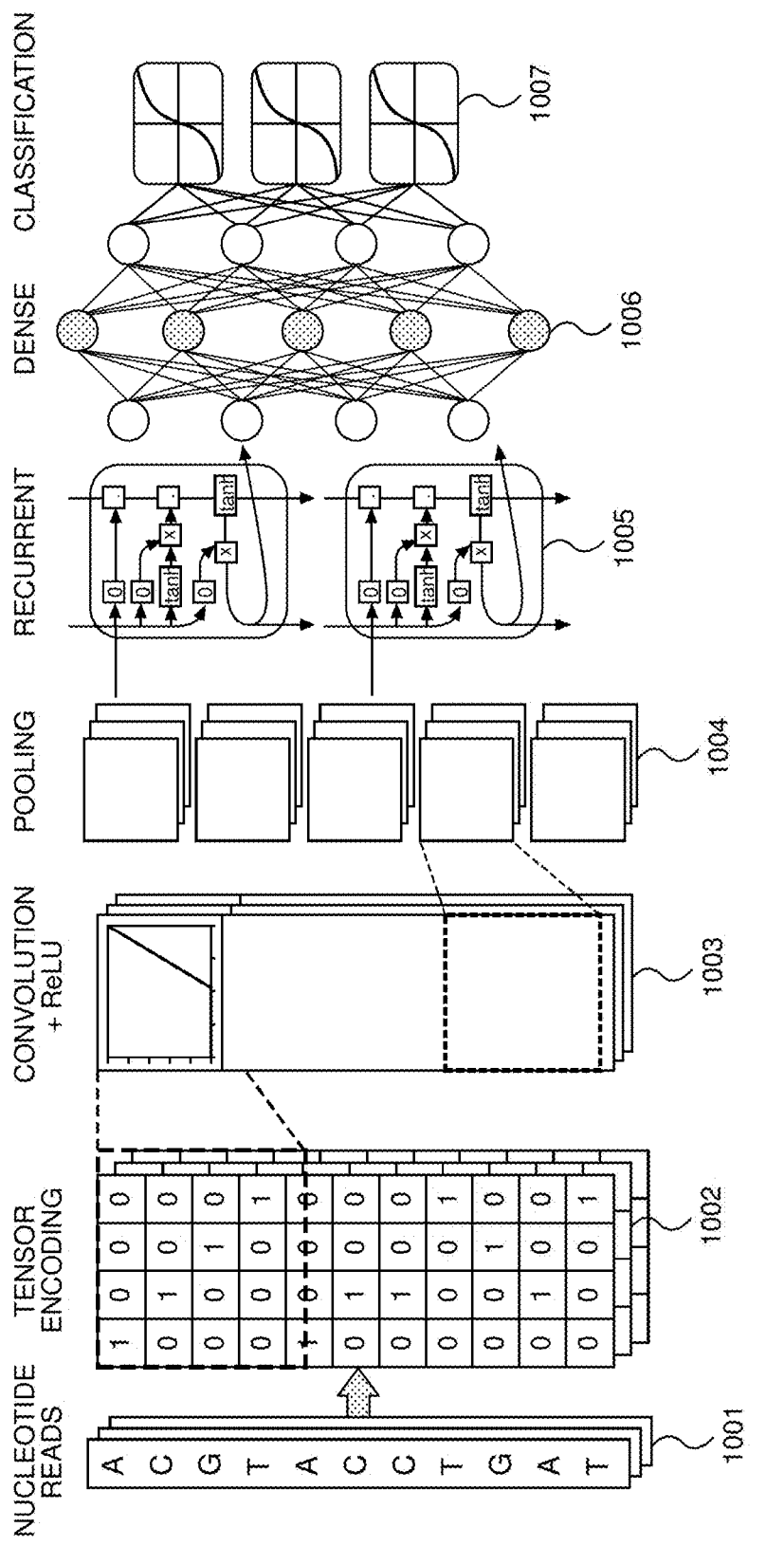
FIG. 10 illustrates an exemplary deep learning neural network, which may be used in one embodiment.

FIG. 10 illustrates an exemplary deep learning network 1000 for identifying variant genes. RNA reads 1001, tensor 1002, CNN 1003, pooling layer 1004, RNN 1005, dense neural network 1006 and classification layer 1007 are illustrated. Tensor 1002 may comprise a multi-dimensional matrix where each 4-bit row represents a single nucleotide encoded in a 4-bit encoding scheme. The rows sequentially define the nucleotide sequence of the RNA read 1001.

In an embodiment, CNN 1003 may include any of a variety of activation functions. In one embodiment, the activation function of the CNN 1003 is a Rectified Linear Unit (ReLU). Alternatively, other activation functions may be used. In an embodiment, pooling layer 1004 may receive the output from CNN 1003 and process it before producing output to RNN 1005. The pooling layer 1004 may be configured to reduce the dimensionality of the data between the CNN 1003 and RNN 1004. In an embodiment, a pooling layer may operate on a window of an output activation map from the CNN 1003 (e.g., a 2×2 window) with a set stride and perform a function to produce a single value from the values in the window. For example, the function performed may be a maximum value function, where the maximum value is selected, or an averaging function, which computes the average. The pooling layer reduces the dimensionality of the data based on the window size and stride length.

Dense neural network 1006 may comprise a densely connected neural network, such as a fully-connected neural network. In a densely connected neural network, most of the nodes in a layer are connected each of the nodes in the following layer. Dense neural network 1006 may comprise a feed forward neural network. Multiple instances of the deep learning neural network 1000 can be trained to classify RNA reads 1001 into known gene classes. In some embodiments, each instance of the deep neural network 1000 can be trained to identify a single gene class for a given RNA read. Other instances of the deep neural network 1000 can be trained to identify RNA reads originating from nonhuman sources, such as bacteria DNA, viruses or contaminants. As described earlier, the deep learning neural network 1000 is only one example of machine learning techniques that can be used to classify unmatched RNA reads. Other examples of machine learning techniques which can be used include, SVM, LDA and Markov chain. A combination of these techniques can also be used.

VI. Assembly

Figure 11:
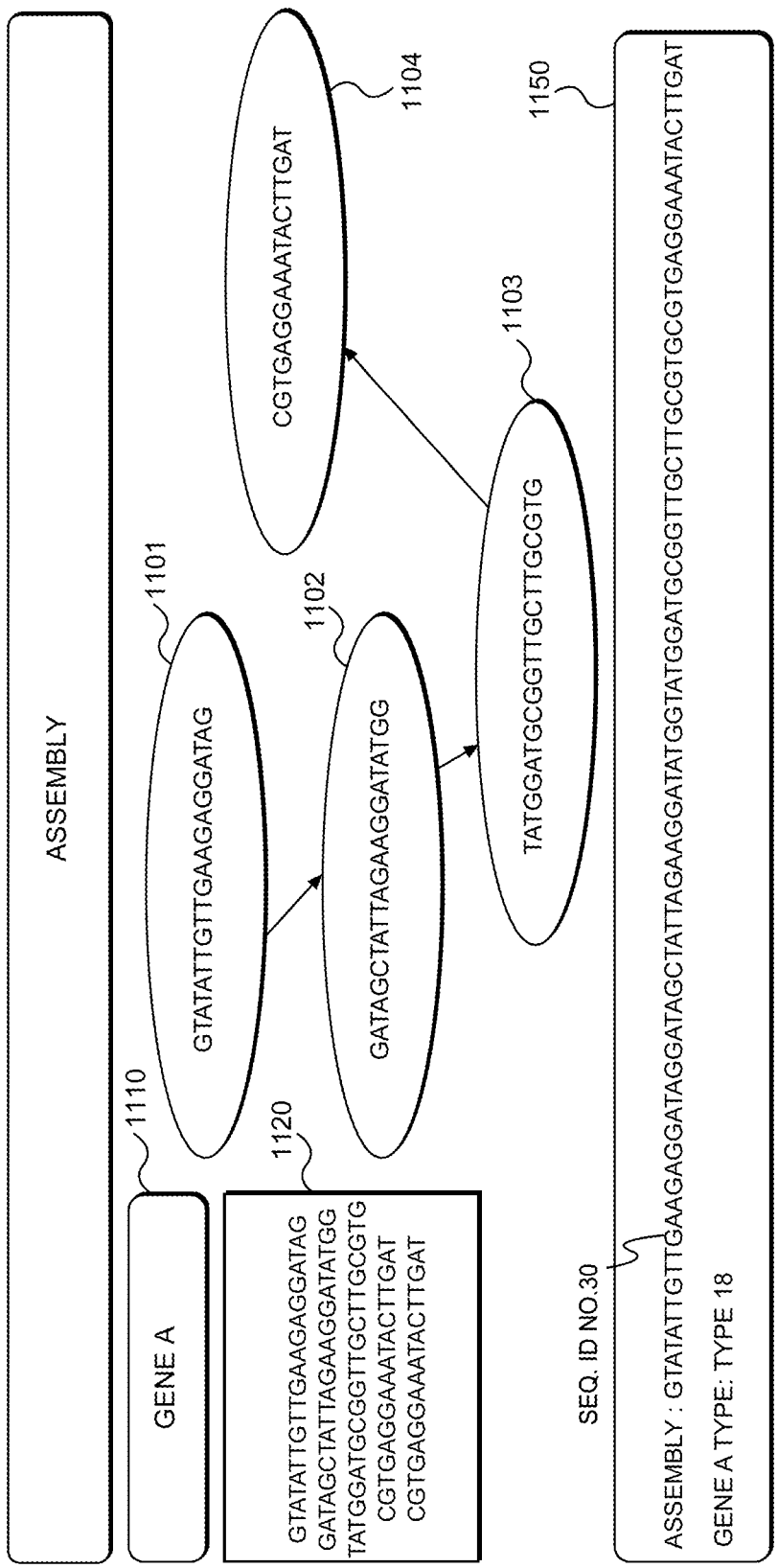
FIG. 11 illustrates an exemplary assembly process, which may be used in one embodiment.

FIG. 11 illustrates an exemplary assembly step. In the exemplary assembly step, RNA reads that correspond to the same RNA transcript or gene or gene family are reassembled into RNA transcripts. As described earlier, the assembly step can be performed on the outcome of RNA reads mapped by the plurality neural networks and/or some RNA reads that are identified using other described methods. The reconstruction provides an indication of the presence and quantity of RNA transcripts in the sample. The resulting reconstruction may not be exact due to errors and alterations performed during high-throughput sequencing.

In one embodiment, RNA reads that correspond to the same RNA transcript or gene or gene family are assembled by identifying nucleotide sequences on either end of the RNA read that overlap with a nucleotide sequence of another RNA read. The overlap is determined by finding matching nucleotide sequences. In some embodiments, the overlapping sequences must be identical. In another embodiment, small differences in the overlapping sequences are allowed to account for mutations and errors in sequencing.

RNA reads 1101, 1102, 1103, and 1104 correspond to the same gene 1110 that corresponds to RNA transcript 1120. The RNA reads 1101, 1102, 1103, and 1104 have overlapping sequences. For example, RNA read 1101 ends with sequence GATAG, which overlaps with the same sequence of RNA read 1102. RNA read 1102 also overlaps with RNA read 1103 with the sequence TATGG. The RNA reads are assembled into sequence 1150 by connecting them at their overlapping sequence portions.

The resulting transcriptome comprising RNA transcripts may comprise on the order of 10,000 RNA transcripts or genes and corresponding quantities.

In other embodiments, a method of assembly utilizing a De Bruijn graph and alignment process is utilized. First, an index, reference or dictionary file of known RNA transcripts are obtained. The known RNA transcripts can be obtained from a variety of sources including, from the NCBI, as described earlier. The RNA transcripts are turned into a De Bruijn graph. The RNA reads are walked along nodes and edges of the De Bruijn graph and compared with the index file until a confident match is found. Further details of this type of RNA transcript identification is outlined in relation to the embodiment of FIG. 12. The classifications outputted by the plurality of machine learning algorithms (for example those described in relation to FIG. 10), and associated with the RNA reads, can be used to resolve ambiguities that might arise as the RNA reads (or portions thereof) are walked along the edges of the De Bruijn graph. Additionally, as described earlier, the strength of node connections can also be used to further identify and reconstruct RNA reads belonging to a known class (as identified by the plurality of the machine learning processes). Consequently, RNA reads in machine learning (ML) identified classes can be reconstructed into their originating RNA transcripts with a high degree of specificity.

The reconstructed RNA transcripts can be further identified by comparing them to known gene types to further identify the reconstructed RNA transcripts with a finer degree of specificity. For example, the plurality of ML processes, as described above and in relation to FIG. 10, might classify a group of RNA reads as MR (killer-cell immunoglobulin-like receptor) genes. The assembly and reconstruction of the ML-classified RNA reads (for example, using De Bruijn and alignment assembly) can further identify which kind of MR genes these RNA reads belong to, and finally the comparison with known gene types can reveal which type of MR genes the RNA reads belong to. RNA transcripts of the human genome can include enormous diversity and this high level of specificity can offer insights and value into treatment of diseases. Genes or patterns of genes of interest to disease analysis and treatment can be found in any number of those diverse DNA expressions.

Figure 12:
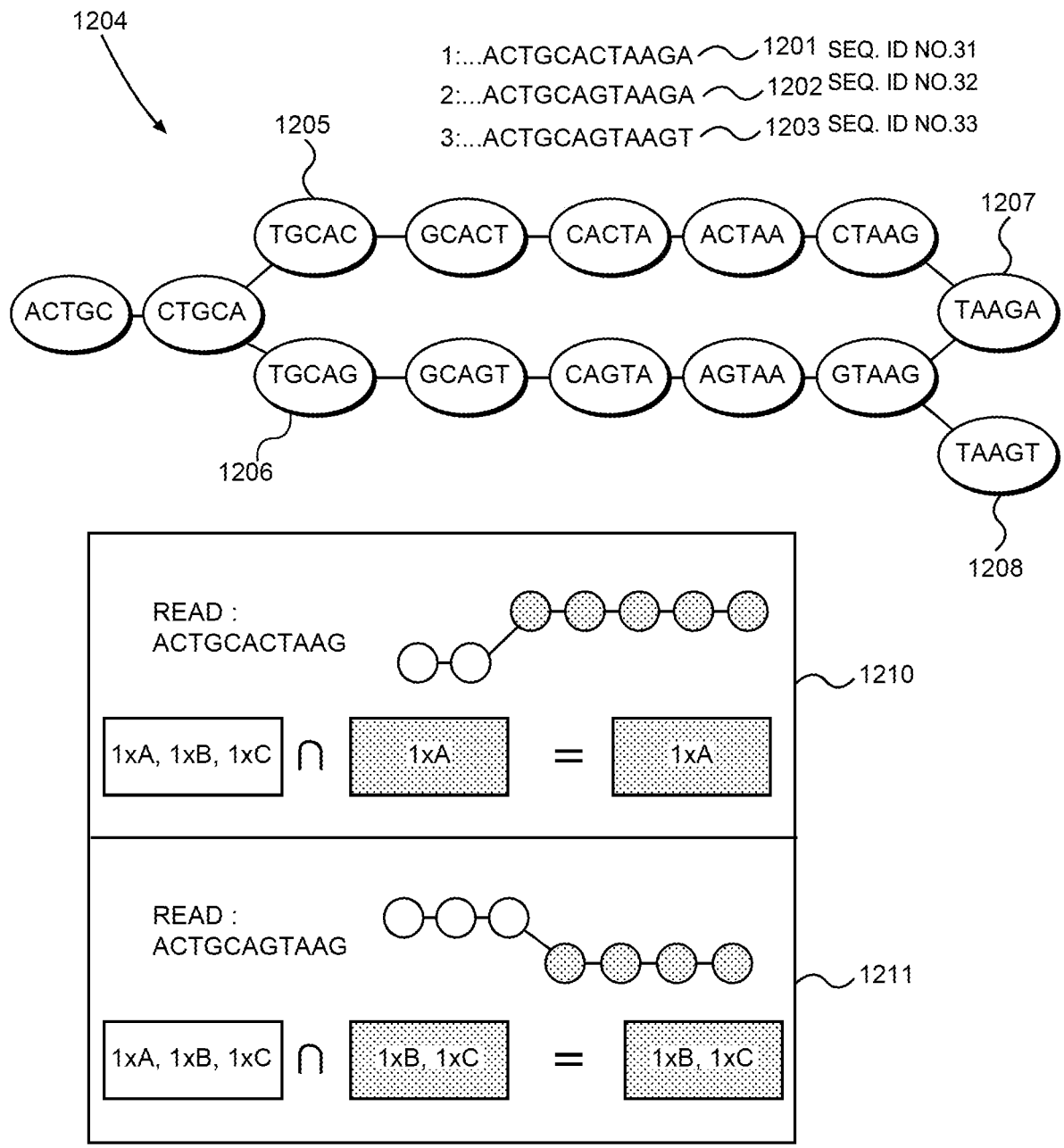
FIG. 12 illustrates an exemplary De Bruijn graph, which may be used in one embodiment.

FIG. 12 illustrates an exemplary method 1204 for matching RNA reads with known RNA transcripts, using a modified De Bruijn graph. The method may be used for quantification, such as steps 102, 102a and also assembly, such as step 104. The method 1204 may use a graph represented by nodes and edges. In an embodiment, a graph is represented in a computer by a matrix of edges or by a set of node and edge objects. In one embodiment, the method 1204 is a De Bruijn graph where the nodes represent K-mers, in other words RNA sequences of length K, and edges exist between K-mers that potentially follow each other in an RNA sequence. In an embodiment, each node contains one or more reference indicating the RNA transcripts that contain the K-mer and also an indication of how far away the next branch in the graph is. A series of sequential edges shows that the chain of K-mers may only belong to a single RNA transcript. However, a branch indicates that the K-mer may belong to one of a plurality of RNA transcripts, and the identity of the RNA transcript might be deduced based on the next nucleotide in the sequence, which causes the identification of the RNA transcript to branch.

The method 1204 represents a K-mer graph with K-mer size of 5. Matching of the RNA read CTGCAGTAAGT to a known RNA transcript, using the method 1204 is illustrated. As an example, the method 1204 uses three reference RNA transcripts 1201, 1202, and 1203 from a database of known RNA transcripts.

In a first step, the program reads K-mer CTGCA, which matches each of the RNA transcripts 1201, 1202, 1203. The node indicates that the next lookup step is one space away. Based on this determination, the program may then read the K-mer one space away.

In a second step, the program reads K-mer TGCAG. As shown in boxes 1210, 1211, the K-mer matches node 1206 and does not match 1205. Therefore, the RNA transcript 1201 may be eliminated as a candidate, but RNA transcripts 1202, 1203 remain candidates. The node indicates that the next lookup step is five spaces away. Based on this determination, the program may then read the K-mer five spaces away.

In a third step, the program reads K-mer TAAGT. This eliminates RNA transcript 1202 and leaves only RNA transcript 1203 remaining. The program determines that the corresponding RNA transcript is transcript 1203. The process of the method 1204 may stop.

In an embodiment, statistical methods may be applied to determine the RNA transcripts that are present when the mapping from an RNA read to an RNA transcript is ambiguous. Maximum likelihood estimation (MLE) and Bayesian approaches may be used. For example, MLE may be used to determine the likelihood that an RNA read belongs to an RNA transcript based on the expression levels of the present RNA transcripts and the conditional probability of the RNA read being detected based on the expression of the RNA transcript. In an embodiment, an existing expression level of each reference RNA transcript is computed or provided from storage or analysis of other RNA read data sets. Alternatively, a random expression level is used. Regardless of the method used for obtaining expression levels, the MLE updates the expression levels through an iterative process until the generated expression levels stabilize. Moreover, the likelihood that the RNA read is present when the corresponding RNA transcript is expressed is provided. Based on this, and based on the presence of an RNA read, the probability that the RNA read belongs to a particular transcript may be calculated as:

Odds of Transcript=Expression Level*$P$(Transcript|RNA Read)

The ratio of each transcript may then be calculated by dividing the odds of the transcript by the sum of the odds of all transcripts. From the ratio, a raw count of the RNA transcript may be calculated by multiplying the ratio by the number of RNA reads that are ambiguous.

An expression level of the transcript may then be calculated by determining the estimated amount of each RNA transcript in the sample. The process may then be repeated using the new expression level. The process is repeated until it converges In an example, two possible genes expressed, A and B with corresponding RNA transcripts. Both share a subsegment of 500 nucleotides, gene A is 1000 nucleotides long, while B is 1500. The probability of the subsegment being present in a sequence read given A being expressed is ½, or $P$ (A|subsegment)=½, while $P$ (B|subsegment)=¼.

In the example, the transcriptome comprises 1000 reads. The initial assumed gene expression is that 50% are from A, and 50% from B. After reading the transcriptome, the program determines that 500 are from A, 200 from B, and 300 that may be A or B. Based on our initial estimation, the odds of A and B are calculated as:

$A: ½*0.5=0.25$ $B: ⅓*0.5=0.17$

Ratio of $A$ in $A/B=0.25/(0.17+0.25)=0.6$

Ratio of $B$ in $A/B=0.17/(0.17+0.25)=0.4$

So, of the 300 A/B reads, it is calculated that 180 are from A, and 120 from B. The result is a total of 680 reads from A, and 320 from B. The new estimated expression levels are 68% A and 32% B.

The program repeats the above calculation using the new estimated expression level of 0.68 and 0.32:

$A: ½*0.68=0.34$ $B: ⅓*0.32=0.107$

Ratio of A in A/B=0.34/(0.34+0.107)=0.76

Ratio of B in A/B=0.107/(0.34+0.107)=0.24%

% A=500+(300*0.76)=728 reads=72.8%

% B=200+(300*0.24)=272 reads=27.2%

The calculation is repeated until the estimation expression level stabilizes, where the change in estimated expression level changes very little. In the example, in the first round, the estimations changed 26%, and the second round only 3.2%.

The likelihood estimations derived above correspond to relative abundances of RNA transcripts in a patient sample compared to one another. Initial probability assumptions can come from study of other databases. Those studies can introduce biases. Averaging techniques can be used to cancel out those biases. Additionally, MLE is not the only method of arriving at the probabilities. In one embodiment, Bayesian methods can be used to generate the relative abundances.

VII. Machine Learning

The preceding steps relate to reconstructing the RNA transcriptome of a single sample and/or in combination with generating a list of relative abundances of RNA transcripts in the sample. These processes can be repeated for a plurality of patients and patient samples. A machine learning step is used to identify factors that drive disease or drive treatment response. In an embodiment, a plurality of RNA transcriptomes are provided, each corresponding to a patient, and an indication of whether the patient suffers from a disease or VITR condition is also provided. A machine learning classifier is then trained on this data, so that the classifier predicts the existence of the disease or VITR condition based on an RNA transcriptome.

Figure 13:
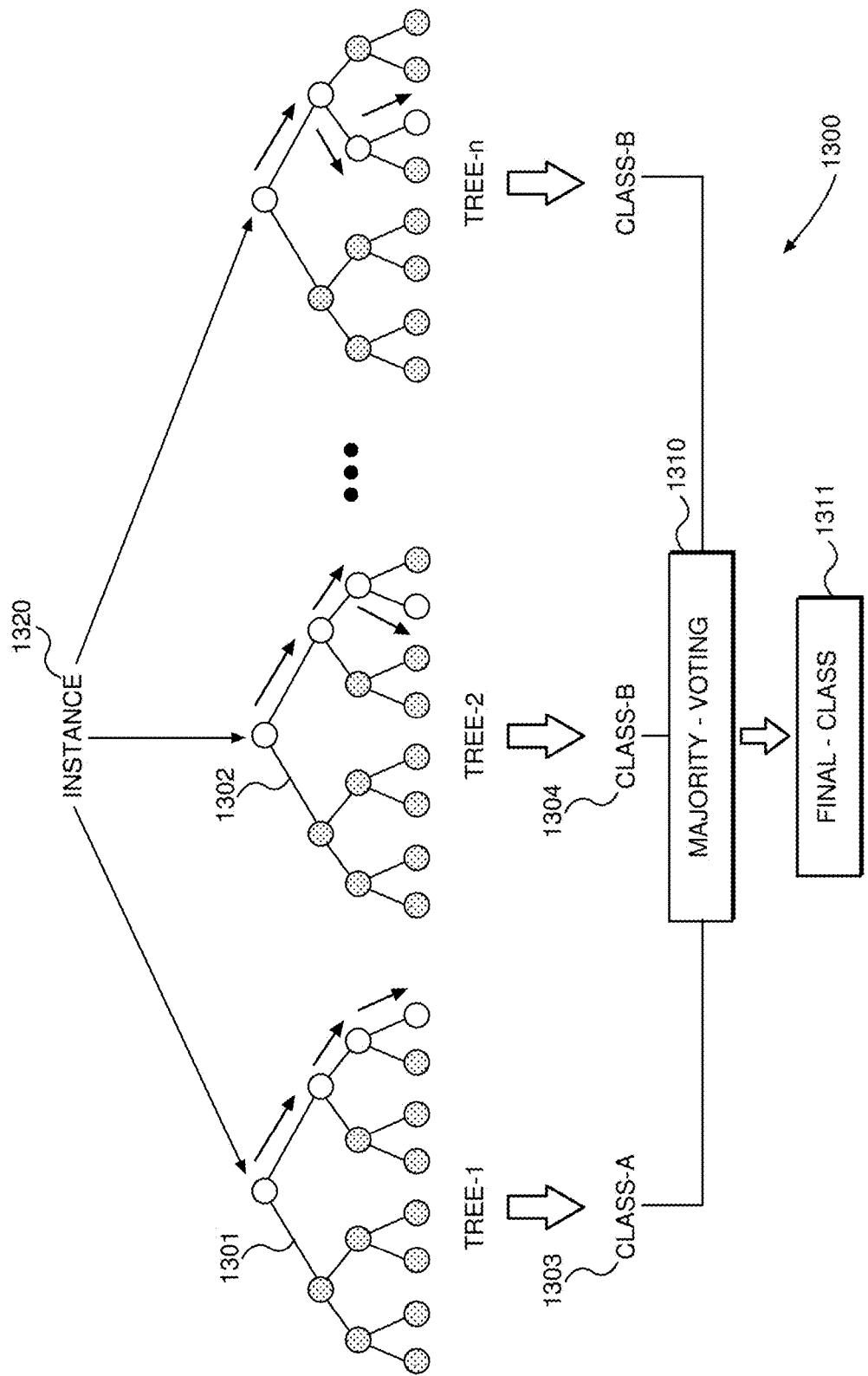
FIG. 13 illustrates an exemplary random forest, which may be used in one embodiment.
Figure 14A:
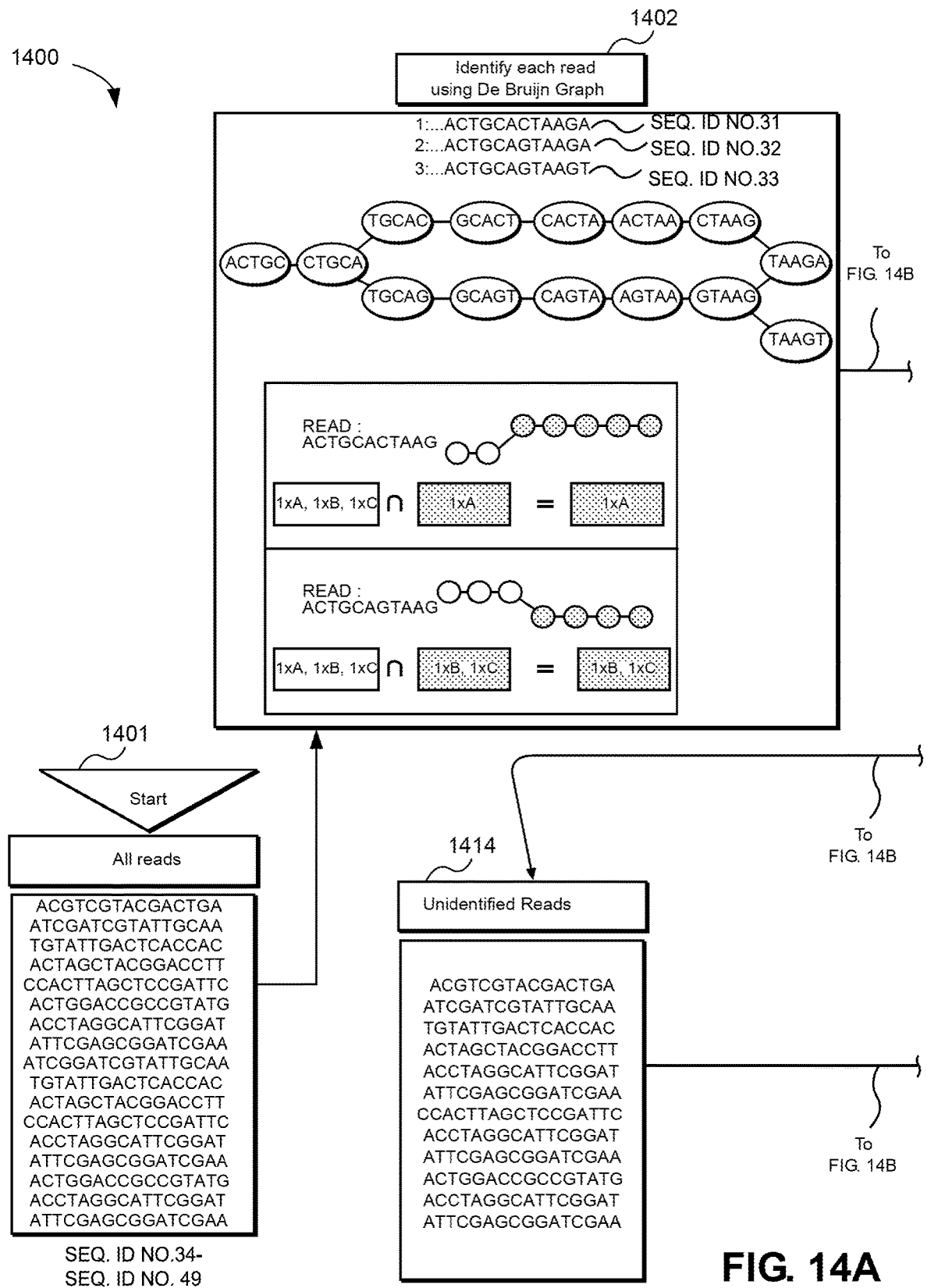
FIG. 14 illustrates an exemplary flow chart of generating a list of labeled, quantified, and annotated RNA transcripts in a patient.
Figure 14B:
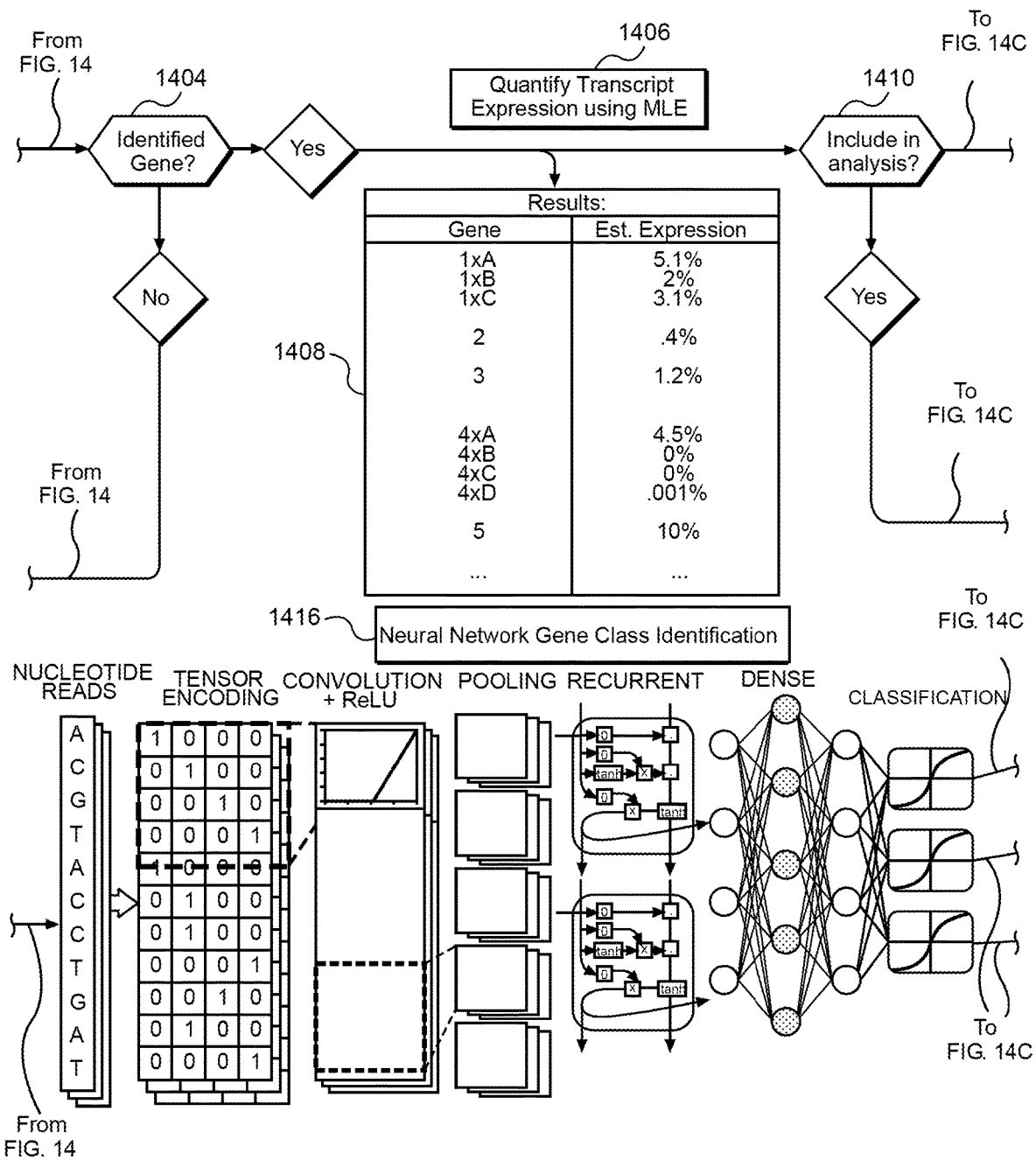
Figure 14C:
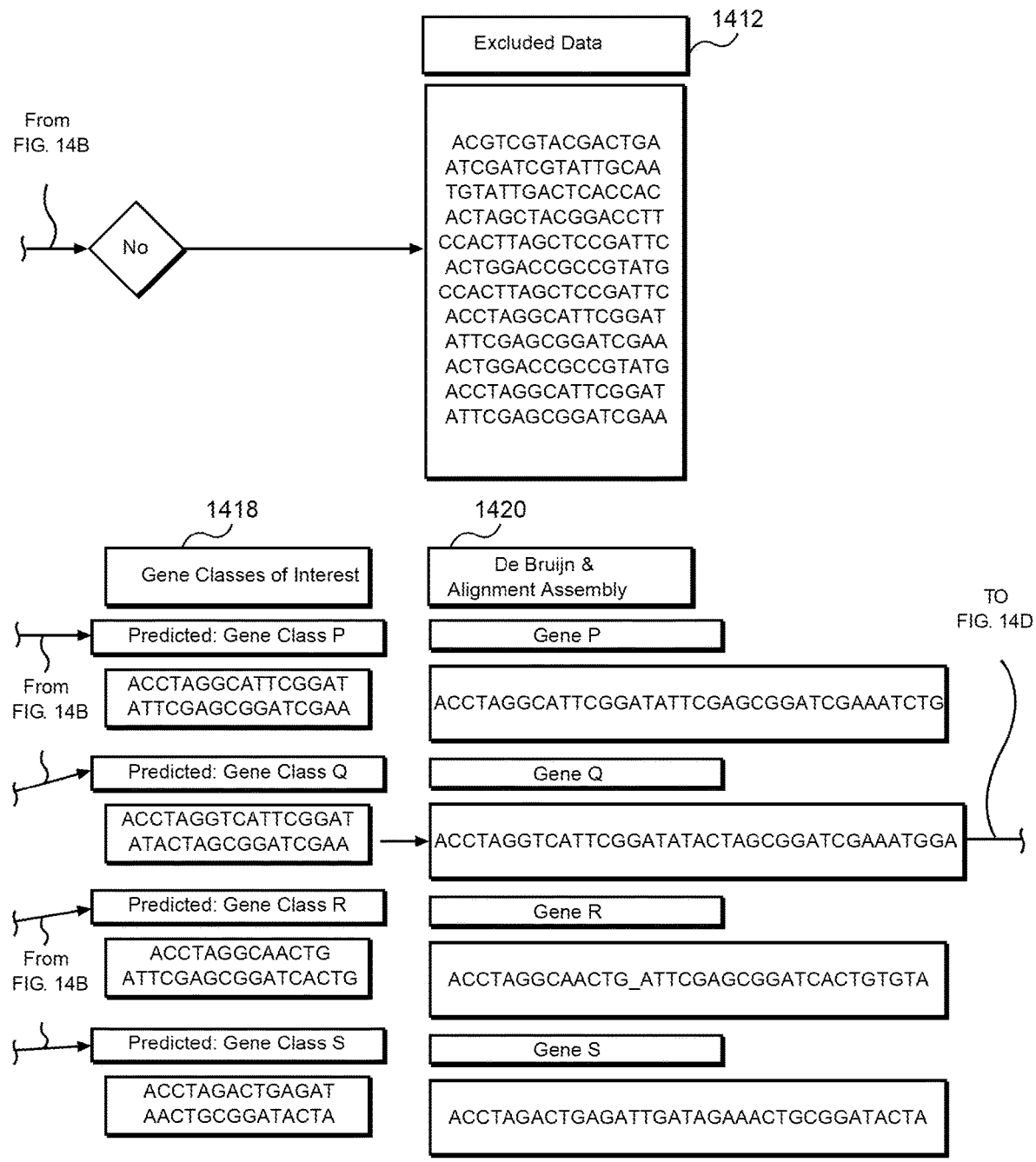
Figure 14D:
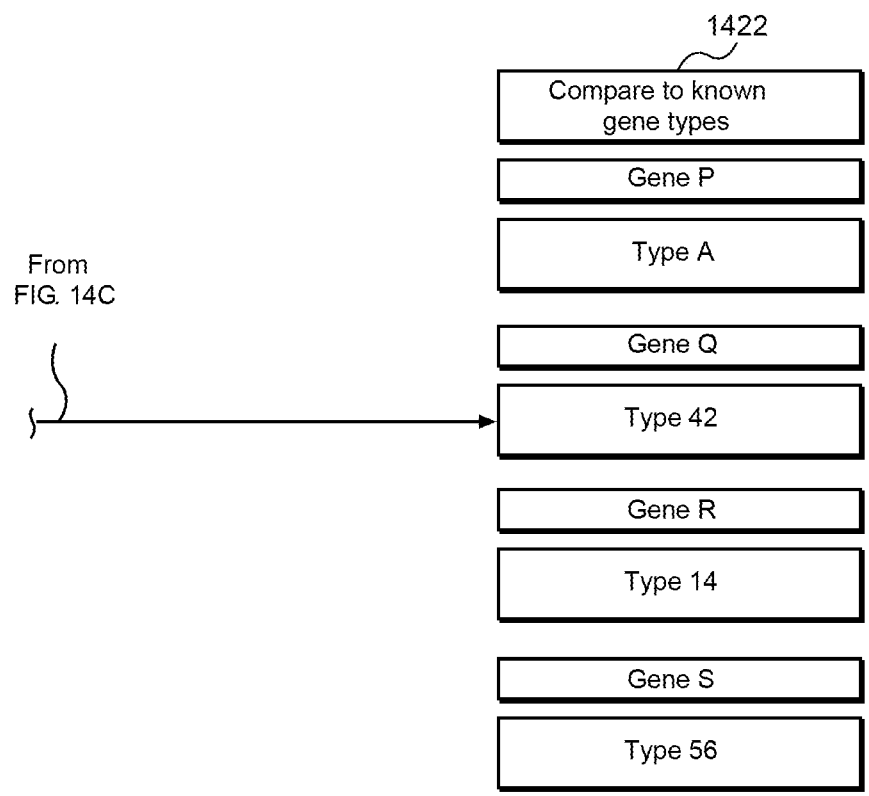

FIG. 13 illustrates an exemplary random forest, which is one machine learning classifier that may be used. One method that may be used to generate the random forest is as follows. A series of iterations are performed, and at each iteration a new tree of the forest is built. At the start of each iteration, a sample of N training examples is randomly or pseudo-randomly selected from the training set through a process known as bootstrapping. The N training examples form the set of training examples used to build a single tree of the forest. The tree is initialized to a start node where all of the training examples are initially located. For each terminal node of the tree, a set of m variables is randomly or pseudo-randomly chosen from the set of RNA transcripts or genes of the sample (which may be on the order of 10,000). A split is chosen on one of the m variables. The split may correspond to a quantity of an RNA transcript or gene. Two daughter nodes may be generated and training examples with quantities of the RNA transcript or gene that are below the threshold quantity of the split may be assigned to a first daughter node and the training examples with quantities of the RNA transcript or gene that are above the threshold quantity of the split may be assigned to the second daughter node.

The split point may be chosen based on maximizing information gain and reduction of entropy, or by Gini index. The split point is chosen to reduce the error of the classifier.

The process is repeated for a series of iterations until a stopping condition is reached, and the set of trees may be combined into an ensemble classifier. To use the ensemble classifier, an RNA transcriptome is entered as input 1320, where the RNA transcriptome may comprise Results file that contains the data about relative abundance of each RNA transcript. Each of the trees 1301, 1302, 1302n is traversed according to the decision points at each node until a leaf is reached. The RNA transcriptome is evaluated at each node to determine whether it meets the threshold quantity of the specified RNA transcript of the node split point. The result of the determination results in the selection of which path to follow to a daughter node. The leaf that is reached outputs one or more classifications 1303, 1304 and associated probabilities. An overall classification of the ensemble is determined by combining the results of the one or more trees. In an embodiment, majority voting 1310 is used to select the classification chosen by most of the trees to arrive at a final classification 1311.

In an embodiment, an individual tree 1301, 1302 of the random forest may also be used as a classifier. The tree is used as a classifier by inputting an RNA transcriptome 1320 and traversing the tree in the same manner of traversal as in the ensemble classifier. The final leaf node that is reached outputs one or more classifications and associated probabilities. The highest probability classification may be selected as the output 1303, 1304.

The resulting trees of the random forest may be analyzed to identify genes of interest in a disease or VITR and thereby identify potential drug targets. Split points that tend to accurately classify patients into disease/VITR and no disease/VITR categories are candidates for genes that may be markers of the disease or VITR. These split points may be identified by large information gain, large reduction in classifier error, or large change in Gini index.

In particular, analysis may be performed on one or more trees of the random forest. A tree that accurately classifies patients into disease/VITR and no disease/VITR categories potentially has parameters that identify one or more genes of interest in the disease/VITR. The top-most split point may be selected as a good candidate for a biomarker or drug target. Additional split points near the top of the tree may also be selected and considered as candidates for a biomarker or drug target.

FIG. 14 illustrates a diagram of a method 1400 of receiving RNA reads from a patient and generating a Results list comprising one or more of an identification of the genes, a quantification of the genes' expression levels, and further annotation (e.g., kind, type) of the genes expressed in the patient. The expressions of genes in a patient are RNA transcripts. The RNA reads are pieces of the RNA transcripts received out of order from laboratory procedures. Mapping the RNA reads to their originating RNA transcripts and the corresponding genes, along with knowing the clinical statuses (e.g., VITR) of the patients can provide insight into disease analysis, treatment planning and new drug discovery.

At step 1401, RNA reads are received from a patient and processed, for example according to the embodiment of FIG. 6. At step 1402, the RNA reads are used to construct a De Bruijn graph. The RNA reads or portions of them are identified by walking the edges of the De Bruijn graph against a reference RNA transcript dictionary (for example one obtained from the NCBI). Some RNA reads will be confidently identified. A counter of that class of RNA transcript (or its corresponding gene) is incremented accordingly. The details of mapping RNA reads to a known RNA transcript (and consequently its corresponding gene) using a De Bruijn graph for identification (or assembly) is further explained in the embodiment of FIG. 12. At step 1404, RNA reads whose corresponding genes could not be confidently identified, but whose corresponding genes could be identified in terms of likelihood of the presence of that gene proceed to the step 1406 for quantifying expression levels. Embodiment of FIG. 12 can be used to generate the likelihood of expression levels of an identified gene and generate the Results file 1408. The Results file 1408 can further be updated by the counters of genes whose respective classes were confidently identified in the Step 1402.

At step 1410, some genes (and their corresponding RNA reads) can be excluded from further analysis. Exclusion can be for various reasons. For example, some genes happen with common frequency in humans, and they may bear little correlation to disease study or drug discovery (e.g., hemoglobin genes). In other cases, some genes may be confidently identified to be nonhuman and have little relevance to disease study or drug discovery for which the method 1400 may be used. Excluding unneeded data allows the method 1400 to perform more efficiently for data that is relevant to the goals of a disease or drug discovery. Excluded data 1412 may be discarded.

At step 1414, the RNA reads whose genes or gene expression probabilities could not be identified at the step 1402 are collected. At step 1416, the unidentified RNA reads are fed through a plurality of machine learning algorithms, such as neural networks, convolutional neural networks, recurring neural networks, dense neural networks, support vector machines, Markov chains and others. In one embodiment, each machine learning algorithm (or a network of them) can be trained to identify a particular class of genes corresponding to an input RNA read. The operations and details of the machine learning algorithms of step 1416 is further described in relation to the embodiment of FIGS. 9 and 10. The plurality of machine learning algorithms in step 1416 can classify the unidentified RNA reads into DNA classes to which the RNA reads belong. As described earlier, the unidentified RNA reads and their corresponding gene classes can include valuable data related to disease and drug discovery. Consequently, further processing on these RNA reads and their corresponding genes will be performed as will be described in relation to steps 1420-1422. In the example shown, the plurality of ML algorithms of step 1416, categorizes RNA reads into gene classes Q, R and S. The RNA reads in these gene classes will be further processed by assembling them into their originating RNA transcripts and corresponding genes in order to gain more insight into the correlation between gene patterns and VITR. Such insight can be used for further disease study and new drug discovery.

The gene classes resulting from the identified RNA reads (via confident identification or via expression level probabilities of the steps 1402 and 1406) can be further studied by their contribution to the Results file 1408, without assembling their RNA reads into their originating RNA transcripts and the corresponding genes. On the other hand, for some identified RNA reads at steps 1402 and 1406, the method 1400 may go through further processing, including formal assembly into originating RNA transcript and the corresponding gene. In the example shown, gene class P is selected for further processing through steps 1420 and 1422. Gene class P may be chosen because of an external observation of its correlation to a disease or drug under study or to test a hypothesis.

At the step 1418, gene classes of interest and their RNA reads are collected (from the output of the steps 1416, and selectively from the output of the steps 1402 and 1406). Additionally, not all gene classes identified by the ML algorithms of step 1416 proceed to further processing. For example, gene classes related to bacteria, viruses, contaminants and generally gene classes unrelated to the goals of a study can be added to the excluded data 1412, and not proceed with further processing. Further processing steps 1420 and 1422 can provide finer mapping of the classes of genes of interest. For example, a collection of unidentified RNA reads having gone through the ML processing of step 1416 can be identified as belonging to gene class MR. Nonetheless, MR genes (and many other genes) can include finer categories, such as kind and type. The classification at the step 1418 may not include the finer level of categorization at that stage. Further processing steps 1420 and 1422 provide a finer identification of the genes (including kind and type) to which the RNA reads belong.

At step 1420, the RNA reads of the gene classes of interest from step 1418 may be assembled to their originating RNA transcripts. The assembly process can be accomplished by constructing a De Bruijn graph from the RNA reads of the step 1418 and using the classification result of the ML step 1416 to resolve ambiguities that were previously unresolved when walking the De Bruijn graph. The step 1420 can otherwise be similar to the embodiment of FIG. 12. Nonetheless, other methods of assembling RNA reads, such as overlap alignment or exhaustive assembly, stitching, scaffolding or any other method of assembly augmented and aided by the output classifications of the ML algorithms of step 1416 can be used to reconstruct corresponding RNA transcripts, which can convey more information about a gene, including its kind.

At step 1422, the reconstructed RNA transcripts or a portion of them and their corresponding genes can be compared against a database of known gene types to identify additional information about the genes present in a patient, including gene types. The information gleaned from steps 1418, 1420 and 1422 can be used to annotate the corresponding genes in Results file 1408. For example, in one embodiment, the Results file 1408 includes the identification and annotation of genes present in a patient (e.g., their classes, kinds and types) and a quantification of the genes (including e.g., the levels of expressions of the genes).

Machine Learning Classification of Results Files

As described in relation to the embodiment of FIG. 1A, step 105 and the embodiment of FIG. 13, a machine learning classifier can be trained with patient clinical data to produce insight into genes that correlate with a disease or treatment response (success/failure). The output of this machine learning classifier can be used to perform laboratory studies or clinical studies for improving treatment response and/or develop new treatments or drugs. The method 1400 can be repeated for a plurality of patients and the generated Results files can be used in a machine learning classifier to identify correlations between genes and diseases and to identify target genes for further laboratory study and drug discovery. The machine learning classifier will additionally be provided with the clinical status data of each patient whose Results file is also fed through the machine learning classifier. As described above, the variables and steps of the method 1400 can be modified to study various diseases or evaluate VITR for various diseases. The relative abundance estimations in the Results files, as well as patient's clinical data (e.g., VITR data), can be used to gain insight from the Results file.

In some embodiments, machine learning classifier can be used to study the difference between disease states or variation in treatment response (VITR) in a patient population. Both forms of study ("disease/healthy" and "treatment success/failure") can be referred to as "binary classifications."

Of the roughly 60,000 known RNA transcripts expressed in humans, most cell types express between 10,000 to 15,000 RNA transcripts. Few machine learning algorithms are effective at dealing with the extreme dimensionality of the RNA expressions in humans. Furthermore, as many proteins are part of the same chemical or signaling pathways, much of the data from RNA transcripts features high co-linearity, which most algorithms have difficulty processing.

In one embodiment, the machine learning classifier, accepting Results files and patient clinical data as input, can be constructed with a random forest architecture. Random forest algorithms make decisions which maximizes information gain. For example, given that we may know a particular negative response to a treatment is related to one or more gene classes, a random forest classifier can help isolate which attributes within the gene classes are useful to discriminate between the gene classes and identify a gene class, kind and type most correlated with a disease or VITR. In one aspect, the Results files can contain information on a plurality of maps of how a particular disease works in human works. The machine learning classifier can identify which gene patterns (including the pattern's attributes, such as class, kind, type) occur in the plurality of the disease maps with greatest frequency. Those recurring gene patterns shared among many disease maps are candidates for new treatment, new drug discovery and potential further laboratory or clinical study.

Figure 15:
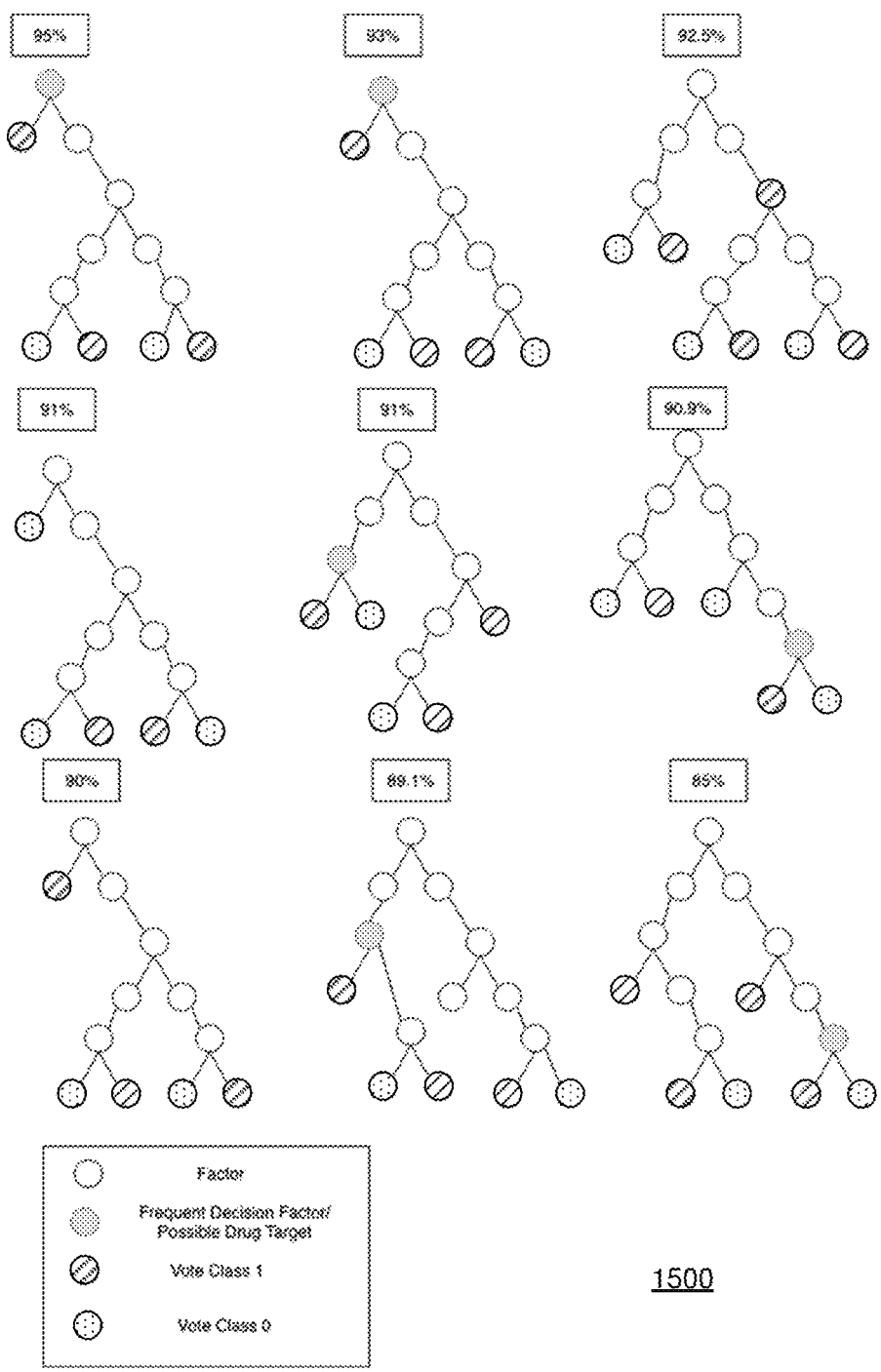
FIG. 15 illustrates an exemplary machine learning classifier, which may be used in one embodiment.

FIG. 15 illustrates an embodiment of the machine learning classifier of step 105 implemented in a random forest (RF) architecture 1500. The random forest 1500 includes a plurality of decision trees. The trees unravel the differentiators of binary classification of data (healthy/unhealthy, success/failure of treatment). For each tree, Entropy $H(X)=-\Sigma[P(X)\log P(X)]$ Information Gain $I(X|Y)=H(X)-H(X|Y)$ Where P(X) is the proportion of the data which is in 1 class. In other words, the tree algorithm chooses a transcript, and an expression level of said transcript which best separates the negative class and positive class most cleanly. The algorithm then chooses the next factor and repeats these splits to a preset depth within the data.

In an embodiment, the trees in random forest 1500 are Gradient Boosted Classifier (GBC) trees, with the accuracy of each tree displayed on top. The GBC trees classify based on a subset of factors. Each decision splits the data into a subset which has more information gain (i.e. each split along the trees better separate the binary classes). The less accurate trees can be iteratively removed from the random forest 1500 and more accurate trees can be left. The decision factors that occur with more frequency among the trees have the most correlation with a disease or VITR and they can indicate RNA transcripts, whose proteins can be potential targets for new drug discovery.

In some embodiments, the method 1400 and the subsequent machine learning classifiers (e.g., the classifier of FIGS. 13 and 15) can be used to identify genes or gene patterns predictive of a disease or VITR. Nonetheless, that is not the only insight that can be gained from the application of the systems and methods described herein. In a preferred embodiment, the method 1400 and the subsequent machine learning step (e.g., random forest or SVM) can be used to identify gene patterns whose manipulation can modify a particular disease and/or VITR. Drug discovery directed to or based on gene patterns that can modify a disease or VITR can lead to discovery of effective and previously unknown drugs and/or treatments. The structure of the described machine learning classifiers and the high degree of specificity of the patients' Results files enable the identification of gene patterns whose manipulation can modify a disease and/or VITR. For example, the random forest structure can be used to identify trees that occur with high degree of robustness (e.g., occur with a high or highest degree of frequency, amongst the trees of the random forest. This robustness can also refer to the trees that have the greatest conserved structure in the forest. These trees contain identification of the gene patterns whose manipulation can modify a particular disease or VITR. In one sense, the described machine learning classifiers built using the Results files and patients' clinical status data, generate a plurality of maps of a disease or VITR and identify gene patterns that recur across the plurality of maps with a high degree of frequency. In some embodiments, the highest occurring gene pattern or a plurality of high recurring gene patterns can be gleaned from the output of the machine learning classifier and used to develop previously unknown drugs targeting these recurring gene patterns.

It is noted that conventional methods may be able to identify gene patterns that are predictive of disease or a patient's response to treatment and may be able to develop drugs that target those genes. However, genes that are predictive of a particular disease may or may not be the genes that can modify the course of the disease and/or influence a patient's response to treatments for the disease. In other words, a biomarker can predict disease or response but may or may not modify the disease or response to treatment of the disease. In some disease cases, top gene patterns predictive of those diseases are not the genes which can most effectively modify the course of those diseases. Or vice versa, in some cases, the gene patterns most effective in improving a patient's response to treatment and/or most effective at slowing or stopping the disease are not the best predictors of that disease. The disclosed systems and methods not only can identify genes that may be predictive of a disease or treatment response, but they can also identify genes or gene patterns that can modify the course of a disease or a patient's response to treatment of that disease.

Identification of genes capable of modifying the disease or patient's treatment response offers a much stronger drug target for improving a patient's response to treatment and/or slowing or stopping the progression of the disease, as opposed to conventional methods that target drugs by identification of biomarkers. For example, some patients are correctly diagnosed using conventional biomarker identification methods, but they respond poorly to treatment. Or some patients can be correctly diagnosed with a disease (e.g., by using conventional biomarker identification techniques), but no treatment for the disease may be known. In such patients, identification of genes and gene patterns capable of modifying the disease or the patient's response to an available treatment can offer more effective treatment options.

Identification of genes capable of modification of the disease or treatment response can be accomplished by employing the described methods and choosing gene patterns that recur with high degree of frequency within the Results files of a plurality of patients. In one embodiment, the machine learning classifier can be used to analyze the plurality of the Results files obtained from a patient population and identify RNA transcripts (or corresponding gene patterns) that occur with high frequency amongst patient population that have either responded poorly to a treatment and/or are diagnosed with a disease for which no known treatment exists. Those high frequency recurring gene patterns comprise gene patterns that are capable of modifying the course of the disease and/or the patient's treatment response in a positive direction. For example, when the machine classifier is implemented with a random forest, high performing trees tend to identify disease predictors, while trees that occur with high frequency tend to be the trees that correspond to gene patterns and/or RNA transcripts that are capable of modifying the disease and/or patient treatment response. Regardless of the type of machine learning classifier used, these classifiers can be implemented to identify the gene patterns and/or the RNA transcripts in the plurality of the Results files that recur with a high degree of frequency. These gene patterns are capable of modifying the disease and/or patient treatment response, and are candidates for development of new drugs and/or treatments.

What is claimed:

1. A computer-implemented method comprising:
providing a list of sequenced RNA reads from a sample of a patient;
providing a dictionary of RNA transcripts;
indexing the list of RNA reads to the dictionary of RNA transcripts to determine for a first plurality of RNA reads a corresponding RNA transcript;
determining for each of a second plurality of RNA reads that there is no corresponding RNA transcript in the dictionary of RNA transcripts;
training a plurality of machine learning classifiers, to output a prediction for a member of a gene family, wherein each of the plurality of machine learning classifiers comprise at least a convolution neural network and/or a recurrent neural network;
inputting each of the second plurality of the RNA reads into the plurality of machine learning classifiers, each of the plurality of machine learning classifiers outputting a prediction of whether the RNA read is a member of a gene family, and assigning two or more of the second plurality of the RNA reads to a highest probability gene family based on the outputs of the plurality of machine learning classifiers;
assembling one or more RNA transcripts of the second plurality of RNA reads based on two or more of the second plurality of RNA reads mapping to the same gene family and having an overlapping sequence of nucleotides;
generating a set of RNA transcript expression levels based on the corresponding RNA transcripts of the first plurality of RNA reads and the assembled RNA transcripts of the second plurality of RNA reads;
creating a training set including the set of RNA transcript expression levels, an indication of whether the patient has a variation in treatment response (VITRO), and data from other patients;
training a response prediction machine learning classifier, based on the training set, to predict the existence of the VITR based on an input set of RNA transcript expression levels; and
using one or more parameters of the response prediction machine learning classifier to identify at least one RNA transcript of interest or gene of interest in the VITR.

2. The method of claim 1, further comprising:
compressing the list of sequenced RNA reads by removing one or more computer-generated labels and converting the list of sequenced RNA reads from a text format to a binary format; and
decompressing the list of sequenced RNA reads from the binary format to the text format.

3. The method of claim 1, wherein the indexing of the list of RNA reads to the dictionary of RNA transcripts is performed using hashing.

4. The method of claim 1, wherein the list of sequenced RNA reads is generated by nucleotide sequencing.

5. The method of claim 1, wherein each of the RNA reads is 100 to 250 nucleotides in length.

6. The method of claim 1, wherein the response prediction machine learning classifier comprises an ensemble of random forest trees, wherein each of the random forest trees include one or more split points; and
wherein the one or more parameters of the prediction machine learning classifier identifying at least one RNA transcript of interest or gene of interest in the VITR comprises a split point of one of the random forest trees.

7. The method of claim 1, wherein the response prediction machine learning classifier comprises a random forest and the random forest is generated by a method comprising:
drawing a sample of training examples from the training set;

generating a random forest tree by creating a tree start node and, for each terminal node of the random forest tree selecting a subset of features of interest, where each feature of interest is an RNA transcript or gene family, selecting a split point among the subset of features of interest where the split point corresponds to a quantity of the RNA transcript or gene family feature of interest, creating at least two daughter nodes of the terminal node, and repeating the process of splitting terminal nodes until a stopping condition is reached; and wherein the one or more parameters of the response prediction machine learning classifier identifying at least one RNA transcript of interest or gene of interest in the VITR comprises a split point of one of the random forest trees.

8. A computer-implemented method comprising:

providing a list of sequenced RNA reads from a sample of a patient;

providing a dictionary of RNA transcripts;

indexing the list of sequenced RNA reads to the dictionary of RNA transcripts to determine for a first plurality of RNA reads a corresponding RNA transcript;

training one or more machine learning classifiers, to output a prediction for a member of a gene family, wherein each of the plurality of machine learning classifiers comprise at least a convolution neural network and/or a recurrent neural network;

matching a second plurality of the RNA reads to a gene family by inputting each of the second plurality of the RNA reads into the one or more machine learning classifiers and receiving a gene family prediction from each of the one or more machine learning classifiers;

assembling one or more RNA transcripts of the second plurality of RNA reads based on two or more of the second plurality of RNA reads mapping to the same gene family and having an overlapping sequence of nucleotides;

creating a training set including the set of RNA transcript expression levels, an indication of whether the patient has a VITR, and data from other patients;

training a response prediction machine learning classifier, based on the training set, to predict the existence of the VITR; and using one or more parameters of the response prediction machine learning classifier to identify at least one RNA transcript of interest or gene of interest in the VITR.

9. The method of claim 8, further comprising:

compressing the list of sequenced RNA reads by removing one or more computer-generated labels and converting the list of sequenced RNA reads from a text format to a binary format; and decompressing the list of sequenced RNA reads from the binary format to the text format.

10. The method of claim 8, wherein the indexing of the list of RNA reads to the dictionary of RNA transcripts is performed using hashing.

11. The method of claim 8, wherein the list of sequenced RNA reads is generated by nucleotide sequencing.

12. The method of claim 8, wherein each of the RNA reads is 100 to 250 nucleotides in length.

13. The method of claim 8, wherein the response prediction machine learning classifier comprises an ensemble of random forest trees, wherein each of the random forest trees include one or more split points; and wherein the one or more parameters of the response prediction machine learning classifier identifying at least one RNA transcript of interest or gene of interest in the VITR comprises a split point of one of the random forest trees.

14. The method of claim 8, wherein the response prediction machine learning classifier comprises a random forest and the random forest is generated by a method comprising:

drawing a sample of training examples from the training set;

generating a random forest tree by creating a tree start node and, for each terminal node of the random forest tree selecting a subset of features of interest, where each feature of interest is an RNA transcript or gene family, selecting a split point among the subset of features of interest, where the split point corresponds to a quantity of the RNA transcript or gene family feature of interest, creating at least two daughter nodes of the terminal node, and repeating the process of splitting terminal nodes until a stopping condition is reached; and wherein the one or more parameters of the response prediction machine learning classifier identifying at least one RNA transcript of interest or gene of interest in the VITR comprises a split point of one of the random forest trees.

15. A computer-implemented method comprising:

providing a list of sequenced RNA reads from a sample of a patient;

providing a dictionary of RNA transcripts;

indexing the list of RNA reads to the dictionary of RNA transcripts to determine for each of a first plurality of RNA reads a corresponding RNA transcript;

training one or more machine learning classifiers, to output a prediction for a member of a gene family, wherein each of the one or more machine learning classifiers comprise at least a convolution neural network and/or a recurrent neural network;

matching a second plurality of the RNA reads to a gene family by inputting each of the second plurality of the RNA reads into the one or more machine learning classifiers and receiving a gene family prediction from each of the one or more machine learning classifiers; and assembling two or more RNA transcripts of the second plurality of RNA reads based on one or more of the second plurality of RNA reads mapping to the same gene family and having an overlapping sequence of nucleotides.

16. The method of claim 15 further comprising:

creating a training set including a set of RNA expression levels for a plurality of patients and an indication for each of the plurality of patients of whether the patient has a variation in treatment response (VITR);

training a response prediction machine learning classifier, based on the training set, to predict the existence of a variation in treatment response (VITR); and using one or more parameters of the response prediction machine learning classifier to identify at least one RNA transcript of interest or gene of interest in the VITR.

17. A computer-implemented method comprising:

reading a text file comprising a list of sequenced RNA reads from a patient;

matching at least one of the RNA reads to a corresponding RNA transcript in a dictionary of RNA transcripts;

training a machine learning classifier, to output a prediction for a member of a gene family, wherein the machine learning classifier comprises at least a convolution neural network and/or a recurrent neural network;

matching at least two of the RNA reads to a gene family by inputting the at least two of the RNA reads to the machine learning classifier and receiving a prediction from the machine learning classifier, wherein the machine learning classifier comprises at least a convolution neural network and/or a recurrent neural network;

assembling two or more RNA reads that match the same gene family by identifying matching nucleotide sequences of the RNA reads, wherein the assembling creates a plurality of RNA transcripts;

training a response prediction machine learning classifier based on the plurality of RNA transcripts and an indication of whether the patient has a variation in treatment response (VITR) and data of other patients; and identifying a parameter of the machine learning classifier that corresponds to an RNA transcript or gene that has an effect on expression of the VITR.

18. A method comprising:
receiving RNA reads from a patient;
mapping RNA reads to transcript expressions;
generating a first, second, and third plurality of RNA reads, wherein the first plurality of RNA reads comprise RNA reads matched to an RNA transcript, the second plurality of RNA reads comprise RNA reads matched to two or more RNA transcripts, and the third plurality of RNA reads comprise unmatched RNA reads;
training a plurality of machine learning algorithms, wherein each machine learning algorithm is trained to receive an RNA read and output a gene classification for the RNA read;
using the plurality of trained machine learning algorithms, classifying the unmatched RNA reads into a plurality of gene classes, wherein the trained machine learning algorithms comprise at least a convolution neural network and/or a recurrent neural network;
assembling the classified unmatched RNA reads into their originating RNA transcripts;
identifying a gene associated with the assembled RNA transcripts;
generating RNA expression level likelihoods for the first, second, and third plurality of RNA reads; and
generating a patient result list comprising:
a first list, comprising genes associated with the first plurality of RNA reads and their corresponding expression level likelihoods;
a second list, comprising genes associated with the second plurality of RNA reads and their corresponding expression level likelihoods; and
a third list, comprising genes associated with the third plurality of RNA reads and their corresponding expression level likelihoods.

19. The method of claim 18, wherein generating RNA expression levels for the second plurality of RNA reads comprises:
constructing a De Bruijn graph with the second plurality of RNA reads;
walking the De Bruijn graph for each RNA read in K-mer subsections;
comparing the K-mer subsections against a list of reference RNA transcripts; and
using a maximum likelihood estimation (MLE) analysis to generate the RNA transcript expression level likelihoods for the second plurality of RNA reads.

20. The method of claim 18, further comprising:
receiving RNA reads from a plurality of patients;
receiving clinical status data of each patient, the clinical status data comprising success or failure to respond to treatment;
generating a patient result list for each patient;
inputting each patient's clinical status data and each patient's patient result list into a machine learning classifier; and
identifying gene patterns occurring in patients with failure to respond to treatment.

21. The method of claim 18, wherein assembling the classified unmatched RNA reads comprises one or more of exhaustive assembly, matching overlap sections, and scaffolding.

22. The method of claim 18, wherein assembling the classified unmatched RNA reads and the generating RNA transcript expression level likelihoods comprises:
generating a De Bruijn graph using the classified unmatched RNA reads in the class;
walking the De Bruijn graph for each RNA read in K-mer subsections;
resolving ambiguities by using the assigned classes obtained from the machine learning algorithms;
comparing the K-mer subsections against a list of reference RNA transcripts; and
using maximum likelihood estimates (MILE) or Bayesian methods to generate the RNA transcript expression level likelihoods for the RNA reads.

23. The method of claim 22, wherein the likelihoods are further generated by choosing nodes in the De Bruijn graph.

24. The method of claim 18, further comprising comparing genes corresponding to the assembled RNA transcripts to gene types to identify types of genes associated with the assembled RNA transcripts.

* * * * *

SEQUENCE LISTING

```
<160> NUMBER OF SEQ ID NOS: 50

<210> SEQ ID NO 1
<211> LENGTH: 250
<212> TYPE: DNA
<213> ORGANISM: Unknown
<220> FEATURE:
<223> OTHER INFORMATION: Raw Nucleotide Sequence

<400> SEQUENCE: 1
catgaggacc aagccaggtg ggatgggtga gtgtggcttc tggaggaagt ggggacacag      60
gacagcattc tttcctgctg gacctgaccc tgtgtcatgt caccttgcta ccacgagagc     120
atggctggca cgcctgtcag aactccccag accaagctaa gcaaaaatta accaatcagt     180
agagcagcct tcggagtaag ggctaaaatg atgtcctcag ggcctggttt tgctttcctt     240
ccatgtcagt                                                            250

<210> SEQ ID NO 2
<211> LENGTH: 250
<212> TYPE: DNA
<213> ORGANISM: Unknown
<220> FEATURE:
<223> OTHER INFORMATION: Raw Nucleotide Sequence

<400> SEQUENCE: 2
aatgtaaacc gtgcactccc aggaaaatgc agacacagca cgcctctttg ggaccgcggt      60
ttatacttta gaagtgctcg gagcccttcc tccagaccgt tctcccacac cccgctccag     120
ggtctgtgcc cggccctact gcgaacgccg ccgctgggcc ccgaccgccc gggaggcgtc     180
ttgggctcgc cccggagctt cctccctgga gccgcgccct gcacccggcc ttgcccggcc     240
ctagcaggga                                                            250

<210> SEQ ID NO 3
<211> LENGTH: 249
<212> TYPE: DNA
<213> ORGANISM: Unknown
<220> FEATURE:
<223> OTHER INFORMATION: Raw Nucleotide Sequence

<400> SEQUENCE: 3
ggtatcaacg cagagtacat gggagtccga actagtctca ggcttcaaca tcgaatacgc      60
cgcaggcccc ttcgccctat tcttcatagc cgaatacaca aacattatta taataaacac     120
cctcagttcc taggaagatt gtagtggtga gggtgtttat tataataatg tttgtgtatt     180
cggctatgaa gaatagggcg aagggcctgc ggcgtattcg atgttgaagc ctgagactag     240
ttcggactc                                                             249

<210> SEQ ID NO 4
<211> LENGTH: 250
<212> TYPE: DNA
<213> ORGANISM: Unknown
```

<220> FEATURE:
<223> OTHER INFORMATION: Raw Nucleotide Sequence

<400> SEQUENCE: 4

```
gtacatggga gtccgaacta gtctcaggct tcaacatcga atacgccgca ggccccttcg    60
ccctattctt catagccgaa tacacaaaca ttattataat aaacaccctc accactacaa   120
tcttcggtat ggagacatat catataagta atgctagggt gagtggtagg aagttttttt   180
cataggaggt gtatgagttg gtcgtagcgg aatcggggt atgctgttcg aattcataag   240
aacagggagg                                                          250
```

<210> SEQ ID NO 5
<211> LENGTH: 250
<212> TYPE: DNA
<213> ORGANISM: Unknown
<220> FEATURE:
<223> OTHER INFORMATION: Raw Nucleotide Sequence

<400> SEQUENCE: 5

```
gggtatcaac gcagagtaca tgggggacca tgagaatcga acccatccct gagaatccaa    60
aattctccgt gccacctatc acacccctgt ctcttataca catctccgag cccacgagac   120
gtagagggtg tgataggtgg cacggagaat tttggattct cagggatggg ttcgattctc   180
atggtccccc atgtactctg cgttgatacc cctgtctctt atacacatct gacgctgccg   240
acgataaggc                                                          250
```

<210> SEQ ID NO 6
<211> LENGTH: 250
<212> TYPE: DNA
<213> ORGANISM: Unknown
<220> FEATURE:
<223> OTHER INFORMATION: Raw Nucleotide Sequence

<400> SEQUENCE: 6

```
accttacttt aggatggggt gtgataggtg gcacggagaa ttttggattc tcagggatgg    60
gttcgattct catggtcccc catgtactct gcgtctgtct cttatacaca tctccgagcc   120
cacgaacgca gagtacatgg gggaccatga gaatcgaacc catccctgag aatccaaaat   180
tctccgtgcc acctatcaca ccccatccta agtaaggtc tgtctcttat acacatctga   240
cgctgccgac                                                          250
```

<210> SEQ ID NO 7
<211> LENGTH: 250
<212> TYPE: DNA
<213> ORGANISM: Unknown
<220> FEATURE:
<223> OTHER INFORMATION: Raw Nucleotide Sequence

<400> SEQUENCE: 7

```
cccctggccc aacccgtcat ctactctacc atctttgcag gcacactcat cacagcgcta    60
agctcgcacc tgtctcttat acacatctcc gagcccacga gacgtagaag aatctcgtat   120
gccgtgtgcg agcttagcgc tgtgatgagt gtgcctgcaa agatggtaga gtagatgacg   180
ggttgggcca ggggctgtct cttatacaca tctgacgctg ccgacgataa ggctcgtgta   240
gatctcggtg                                                          250
```

<210> SEQ ID NO 8
<211> LENGTH: 250
<212> TYPE: DNA

<213> ORGANISM: Unknown
<220> FEATURE:
<223> OTHER INFORMATION: Raw Nucleotide Sequence

<400> SEQUENCE: 8

```
cacactcatc acagcgctaa gctcgcactg attttttacc tgagtaggcc tagaaataaa      60
catgctagct tttattccag ttctaacctg tctcttatac acatctccga gcccacgaga     120
cgtaggttag aactggaata aaagctagca tgtttatttc taggcctact caggtaaaaa     180
atcagtgcga gcttagcgct gtgatgagtg tgctgtctct tatacacatc tgacgctgcc     240
gacgataagg                                                            250
```

<210> SEQ ID NO 9
<211> LENGTH: 250
<212> TYPE: DNA
<213> ORGANISM: Unknown
<220> FEATURE:
<223> OTHER INFORMATION: Raw Nucleotide Sequence

<400> SEQUENCE: 9

```
tacttgatgg cagcttctgt ggaacgaggg tttatttttt tggttagaac tggaataaaa      60
gctagcatgt ttatttctag gcctactcag gtaaaaaatt gcgagcttag cgctgtgatg     120
agtctactca tcacagcgct aagctcgcaa ttttttacct gagtaggcct agaaataaac     180
atgctagctt ttattccagt tctaaccaaa aaaataaacc ctcgttccac agaagctgcc     240
atcaagtact                                                            250
```

<210> SEQ ID NO 10
<211> LENGTH: 250
<212> TYPE: DNA
<213> ORGANISM: Unknown
<220> FEATURE:
<223> OTHER INFORMATION: Raw Nucleotide Sequence

<400> SEQUENCE: 10

```
tacttgatgg cagcttctgt ggaacgaggg tttatttttt tggttagaac tggaataaaa      60
gctagcatgt ttatttctag gcctactcag gtaaaaaatt gcgagcttag cgctgtgatg     120
agtctactca tcacagcgct aagctcgcaa ttttttacct gagtaggcct agaaataaac     180
atgctagctt ttattccagt tctaaccaaa aaaataaacc ctcgttccac agaagctgcc     240
atcaagtact                                                            250
```

<210> SEQ ID NO 11
<211> LENGTH: 250
<212> TYPE: DNA
<213> ORGANISM: Unknown
<220> FEATURE:
<223> OTHER INFORMATION: Raw Nucleotide Sequence

<400> SEQUENCE: 11

```
gattatggat gcggttgctt gcgtgaggaa atacttgatg cagcttctg tggaacgagg       60
gtttattttt ttggttagaa ctggaataaa agctagcatg tttatttcta ggcctactca     120
ggtaactttg caggcacact catcacagcg ctaagctcgc actgattttt tacctgagta     180
ggcctagaaa taaacatgct agcttttatt ccagttctaa ccaaaaaaat aaaccctcgt     240
tccacagaag                                                            250
```

<210> SEQ ID NO 12
<211> LENGTH: 250

<212> TYPE: DNA
<213> ORGANISM: Unknown
<220> FEATURE:
<223> OTHER INFORMATION: Raw Nucleotide Sequence

<400> SEQUENCE: 12

| | | | | | |
|---|---|---|---|---|---|
| tagaaggatt | atggatgcgg | ttgcttgcgt | gaggaaatac | ttgatggcag | cttctgtgga | 60 |
| acgagggttt | attttttttgg | ttagaactgg | aataaaagct | agcatgttta | tttctaggcc | 120 |
| tactcgatta | atcccctggc | ccaacccgtc | atctactcta | ccatctttgc | aggcacactc | 180 |
| atcacagcgc | taagctcgca | ctgatttttt | acctgagtag | gcctagaaat | aaacatgcta | 240 |
| gcttttattc | | | | | | 250 |

<210> SEQ ID NO 13
<211> LENGTH: 250
<212> TYPE: DNA
<213> ORGANISM: Unknown
<220> FEATURE:
<223> OTHER INFORMATION: Raw Nucleotide Sequence

<400> SEQUENCE: 13

| | | | | | |
|---|---|---|---|---|---|
| ttagaaggat | tatggatgcg | gttgcttgcg | tgaggaaata | cttgatggca | gcttctgtgg | 60 |
| aacgagggtt | tattttttttg | gttagaactg | gaataaaagc | tagcatgttt | atttctaggc | 120 |
| ctactgtaca | tgggattaat | cccctggccc | aacccgtcat | ctactctacc | atctttgcag | 180 |
| gcacactcat | cacagcgcta | agctcgcatt | gattttttac | ctgagtaggc | ctagaaataa | 240 |
| acatgctagc | | | | | | 250 |

<210> SEQ ID NO 14
<211> LENGTH: 185
<212> TYPE: DNA
<213> ORGANISM: Unknown
<220> FEATURE:
<223> OTHER INFORMATION: Raw Nucleotide Sequence

<400> SEQUENCE: 14

| | | | | | |
|---|---|---|---|---|---|
| gtggaacgag | ggtttatttt | tttggttaga | actggaataa | aagctagcat | gtttatttct | 60 |
| ggtatcaacg | cagagtacat | gggattaatc | ccctggccca | acccgtcatc | tactctacca | 120 |
| tctttgcagg | cacactcatc | acagcgctaa | actcgcactg | attttttacc | tgagtaggcc | 180 |
| tagaa | | | | | | 185 |

<210> SEQ ID NO 15
<211> LENGTH: 250
<212> TYPE: DNA
<213> ORGANISM: Unknown
<220> FEATURE:
<223> OTHER INFORMATION: Raw Nucleotide Sequence

<400> SEQUENCE: 15

| | | | | | |
|---|---|---|---|---|---|
| gtatattgtt | gaagaggata | gctattagaa | ggattatgga | tgcggttgct | tgcgtgagga | 60 |
| aatacttgat | ggcagcttct | gtggaacgag | ggtttatttt | tttggttaga | actggaataa | 120 |
| aagctgatta | atcccctggc | ccaacccgtc | atctactcta | ccatctttgc | aggcacactc | 180 |
| atcacagcgc | taagctcgca | ctgatttttt | acctgagtag | gcctagaaat | aaacatgcta | 240 |
| gcttttattc | | | | | | 250 |

<210> SEQ ID NO 16
<211> LENGTH: 11
<212> TYPE: DNA

```
<213> ORGANISM: Artificial Sequence
<220> FEATURE:
<223> OTHER INFORMATION: Synthetic Construct

<400> SEQUENCE: 16
acgtcgccat a                                                          11

<210> SEQ ID NO 17
<211> LENGTH: 11
<212> TYPE: DNA
<213> ORGANISM: Artificial Sequence
<220> FEATURE:
<223> OTHER INFORMATION: Synthetic Construct

<400> SEQUENCE: 17
acgtcgccat g                                                          11

<210> SEQ ID NO 18
<211> LENGTH: 11
<212> TYPE: DNA
<213> ORGANISM: Artificial Sequence
<220> FEATURE:
<223> OTHER INFORMATION: Synthetic Construct

<400> SEQUENCE: 18
acgtcgaaat a                                                          11

<210> SEQ ID NO 19
<211> LENGTH: 11
<212> TYPE: DNA
<213> ORGANISM: Artificial Sequence
<220> FEATURE:
<223> OTHER INFORMATION: Synthetic Construct

<400> SEQUENCE: 19
gggtcgtcat c                                                          11

<210> SEQ ID NO 20
<211> LENGTH: 12
<212> TYPE: DNA
<213> ORGANISM: Artificial Sequence
<220> FEATURE:
<223> OTHER INFORMATION: Synthetic Construct

<400> SEQUENCE: 20
acgtgttaca ta                                                         12

<210> SEQ ID NO 21
<211> LENGTH: 12
<212> TYPE: DNA
<213> ORGANISM: Artificial Sequence
<220> FEATURE:
<223> OTHER INFORMATION: Synthetic Construct

<400> SEQUENCE: 21
acgtcgtacc ta                                                         12

<210> SEQ ID NO 22
<211> LENGTH: 11
<212> TYPE: DNA
<213> ORGANISM: Artificial Sequence
<220> FEATURE:
<223> OTHER INFORMATION: Synthetic Construct

<400> SEQUENCE: 22
ccgtcctcat a                                                          11
```

<210> SEQ ID NO 23
<211> LENGTH: 11
<212> TYPE: DNA
<213> ORGANISM: Artificial Sequence
<220> FEATURE:
<223> OTHER INFORMATION: Synthetic Construct

<400> SEQUENCE: 23
ccgtcgtcat t                                                              11

<210> SEQ ID NO 24
<211> LENGTH: 169
<212> TYPE: DNA
<213> ORGANISM: Artificial Sequence
<220> FEATURE:
<223> OTHER INFORMATION: Synthetic Construct

<400> SEQUENCE: 24
gtatattgtt gaagaggata gctattagaa ggattatgga tgcggttgcg tgaggaaata        60
cttgatggca gcttctgtgg aacgagggtt tatttttttg gttagaactg gaataaaagc       120
tgattaatcc cctggcccaa cccgtcatct acttctacca tctttgcag                   169

<210> SEQ ID NO 25
<211> LENGTH: 171
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (154)..(154)
<223> OTHER INFORMATION: n is a, c, g, t or u

<400> SEQUENCE: 25
gtatattgta gtagaggata gctattagag gatgctggat gcggttgctg gcgcgaggaa        60
atacttgatc gtccttctgt ggaacgaggg tttatttaat tggcgagaac tggaatataa       120
gctgattaat taccctggcc caacccgcca tctnttctac catctttgca g                171

<210> SEQ ID NO 26
<211> LENGTH: 29
<212> TYPE: DNA
<213> ORGANISM: Artificial Sequence
<220> FEATURE:
<223> OTHER INFORMATION: Synthetic Construct

<400> SEQUENCE: 26
gtatattgtt gaagaggata gctattaga                                           29

<210> SEQ ID NO 27
<211> LENGTH: 22
<212> TYPE: DNA
<213> ORGANISM: Artificial Sequence
<220> FEATURE:
<223> OTHER INFORMATION: Synthetic Construct

<400> SEQUENCE: 27
actgtcgtga tacaatagct cc                                                  22

<210> SEQ ID NO 28
<211> LENGTH: 22
<212> TYPE: DNA
<213> ORGANISM: Artificial Sequence
<220> FEATURE:

<223> OTHER INFORMATION: Synthetic Construct

<400> SEQUENCE: 28
tgctatgcat tgtacaccat ac                                         22

<210> SEQ ID NO 29
<211> LENGTH: 11
<212> TYPE: DNA
<213> ORGANISM: Artificial Sequence
<220> FEATURE:
<223> OTHER INFORMATION: Synthetic Construct

<400> SEQUENCE: 29
acgtacctga t                                                     11

<210> SEQ ID NO 30
<211> LENGTH: 83
<212> TYPE: DNA
<213> ORGANISM: Artificial Sequence
<220> FEATURE:
<223> OTHER INFORMATION: Synthetic Construct

<400> SEQUENCE: 30
gtatattgtt gaagaggata ggatagctat tagaaggata tggtatggat gcggttgctt    60
gcgtgcgtga ggaaatactt gat                                         83

<210> SEQ ID NO 31
<211> LENGTH: 12
<212> TYPE: DNA
<213> ORGANISM: Artificial Sequence
<220> FEATURE:
<223> OTHER INFORMATION: Synthetic Construct

<400> SEQUENCE: 31
actgcactaa ga                                                    12

<210> SEQ ID NO 32
<211> LENGTH: 12
<212> TYPE: DNA
<213> ORGANISM: Artificial Sequence
<220> FEATURE:
<223> OTHER INFORMATION: Syntehtic Construct

<400> SEQUENCE: 32
actgcagtaa ga                                                    12

<210> SEQ ID NO 33
<211> LENGTH: 12
<212> TYPE: DNA
<213> ORGANISM: Artificial Sequence
<220> FEATURE:
<223> OTHER INFORMATION: Synthetic Construct

<400> SEQUENCE: 33
actgcagtaa gt                                                    12

<210> SEQ ID NO 34
<211> LENGTH: 15
<212> TYPE: DNA
<213> ORGANISM: Artificial Sequence
<220> FEATURE:
<223> OTHER INFORMATION: Synthetic Construct

<400> SEQUENCE: 34
acgtcgtacg actga                                                 15

```
<210> SEQ ID NO 35
<211> LENGTH: 16
<212> TYPE: DNA
<213> ORGANISM: Artificial Sequence
<220> FEATURE:
<223> OTHER INFORMATION: Synthetic Construct

<400> SEQUENCE: 35
atcgatcgta ttgcaa                                                         16

<210> SEQ ID NO 36
<211> LENGTH: 16
<212> TYPE: DNA
<213> ORGANISM: Artificial Sequence
<220> FEATURE:
<223> OTHER INFORMATION: Synthetic Construct

<400> SEQUENCE: 36
tgtattgact caccac                                                         16

<210> SEQ ID NO 37
<211> LENGTH: 16
<212> TYPE: DNA
<213> ORGANISM: Artificial Sequence
<220> FEATURE:
<223> OTHER INFORMATION: Synthetic Construct

<400> SEQUENCE: 37
actagctacg gacctt                                                         16

<210> SEQ ID NO 38
<211> LENGTH: 17
<212> TYPE: DNA
<213> ORGANISM: Artificial Sequence
<220> FEATURE:
<223> OTHER INFORMATION: Synthetic Construct

<400> SEQUENCE: 38
ccacttagct ccgattc                                                        17

<210> SEQ ID NO 39
<211> LENGTH: 16
<212> TYPE: DNA
<213> ORGANISM: Artificial Sequence
<220> FEATURE:
<223> OTHER INFORMATION: Synthetic Construct

<400> SEQUENCE: 39
actggaccgc cgtatg                                                         16

<210> SEQ ID NO 40
<211> LENGTH: 16
<212> TYPE: DNA
<213> ORGANISM: Artificial Sequence
<220> FEATURE:
<223> OTHER INFORMATION: Synthetic Construct

<400> SEQUENCE: 40
acctaggcat tcggat                                                         16

<210> SEQ ID NO 41
<211> LENGTH: 16
<212> TYPE: DNA
<213> ORGANISM: Artificial Sequence
<220> FEATURE:
```

```
<223> OTHER INFORMATION: Synthetic Construct

<400> SEQUENCE: 41
attcgagcgg atcgaa                                                      16

<210> SEQ ID NO 42
<211> LENGTH: 16
<212> TYPE: DNA
<213> ORGANISM: Artificial Sequence
<220> FEATURE:
<223> OTHER INFORMATION: Synthetic Construct

<400> SEQUENCE: 42
tgtattgact caccac                                                      16

<210> SEQ ID NO 43
<211> LENGTH: 16
<212> TYPE: DNA
<213> ORGANISM: Artificial Sequence
<220> FEATURE:
<223> OTHER INFORMATION: Synthetic Construct

<400> SEQUENCE: 43
actagctacg gacctt                                                      16

<210> SEQ ID NO 44
<211> LENGTH: 17
<212> TYPE: DNA
<213> ORGANISM: Artificial Sequence
<220> FEATURE:
<223> OTHER INFORMATION: Synthetic Construct

<400> SEQUENCE: 44
ccacttagct ccgattc                                                     17

<210> SEQ ID NO 45
<211> LENGTH: 16
<212> TYPE: DNA
<213> ORGANISM: Artificial Sequence
<220> FEATURE:
<223> OTHER INFORMATION: Synthetic Construct

<400> SEQUENCE: 45
acctaggcat tcggat                                                      16

<210> SEQ ID NO 46
<211> LENGTH: 16
<212> TYPE: DNA
<213> ORGANISM: Artificial Sequence
<220> FEATURE:
<223> OTHER INFORMATION: Synthetic Construct

<400> SEQUENCE: 46
attcgagcgg atcgaa                                                      16

<210> SEQ ID NO 47
<211> LENGTH: 16
<212> TYPE: DNA
<213> ORGANISM: Artificial Sequence
<220> FEATURE:
<223> OTHER INFORMATION: Synthetic Construct

<400> SEQUENCE: 47
actggaccgc cgtatg                                                      16
```

```
<210> SEQ ID NO 48
<211> LENGTH: 16
<212> TYPE: DNA
<213> ORGANISM: Artificial Sequence
<220> FEATURE:
<223> OTHER INFORMATION: Synthetic Construct

<400> SEQUENCE: 48
acctaggcat tcggat                                                           16

<210> SEQ ID NO 49
<211> LENGTH: 16
<212> TYPE: DNA
<213> ORGANISM: Artificial Sequence
<220> FEATURE:
<223> OTHER INFORMATION: Synthetic Construct

<400> SEQUENCE: 49
attcgagcgg atcgaa                                                           16

<210> SEQ ID NO 50
<211> LENGTH: 14
<212> TYPE: DNA
<213> ORGANISM: Artificial Sequence
<220> FEATURE:
<223> OTHER INFORMATION: Synthetic Construct

<400> SEQUENCE: 50
tgctatgcat tgta                                                             14
```